(12) United States Patent
Kuduk et al.

(10) Patent No.: US 7,816,380 B2
(45) Date of Patent: *Oct. 19, 2010

(54) 1-HYDROXYCYCLOALKANECARBOXAMIDE DERIVATIVES

(75) Inventors: Scott D. Kuduk, Harleysville, PA (US); Michael R. Wood, Harleysville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 173 days.

This patent is subject to a terminal disclaimer.

(21) Appl. No.: 11/920,306

(22) PCT Filed: May 30, 2006

(86) PCT No.: PCT/US2006/020668

§ 371 (c)(1), (2), (4) Date: Nov. 13, 2007

(87) PCT Pub. No.: WO2006/132837

PCT Pub. Date: Dec. 14, 2006

(65) Prior Publication Data

US 2009/0062349 A1 Mar. 5, 2009

Related U.S. Application Data

(60) Provisional application No. 60/687,469, filed on Jun. 3, 2005.

(51) Int. Cl.
- A61K 31/24 (2006.01)
- C07D 419/00 (2006.01)
- C07D 413/00 (2006.01)

(52) U.S. Cl. .................. 514/340; 546/268.4; 546/269.1
(58) Field of Classification Search .................. 514/340; 546/268.4, 269.1
See application file for complete search history.

(56) References Cited

U.S. PATENT DOCUMENTS

2008/0318976 A1* 12/2008 Wood et al. .................. 514/256

FOREIGN PATENT DOCUMENTS

| WO | WO2004/019868 | 3/2004 |
| WO | 2005063690 | * 7/2005 |
| WO | WO2005/063690 | 7/2005 |

OTHER PUBLICATIONS

Patani et. al., "Bioisosterism: A Rational Approach in Drug Design", Chem. Rev. 1996, 96, 3147-3176.*

* cited by examiner

*Primary Examiner*—Janet L Andres
*Assistant Examiner*—Binta M Robinson
(74) *Attorney, Agent, or Firm*—Mollie M. Yang; Valerie J. Camara

(57) ABSTRACT

α-Hydroxycycloalkanecarboxamide derivatives of formula (I) or a pharmaceutically acceptable salt thereof, wherein formula (a) is a single or double bond; $R^1$, $R^2$ and $R^3$ are each independently selected from H, halogen and OH; or $R^1$ and $R^2$ attached to the same carbon atom together represent oxo; $R^4$ is H or methyl; $R^5$ is Cl or $I^2$; $R^6$ is selected from —$CO_2$—$C_{1-4}$alkyl, —O—$C_{1-4}$alkyl, —O—$C_{1-4}$haloalkyl, 2-methyltetrazol-5-yl, 5-methyl-1,2,4-oxadiazol-3-yl, 3-methyl-1,2,4-oxadiazol-5-yl, 5-halomethyl-1,2,4-oxadiazol-3-yl, 3-halomethyl-1,2,4-oxadiazol-5-yl, tetrazol-5-yl, 5-halomethyl-1,2,3-triazolyl, and 5-methyl-1,2,3-triazolyl; $R^7$ and $R^8$ are each independently Cl or $I^2$; and n is 0 or 1, are bradykinin B1 antagonists or inverse agonists useful in the treatment or prevention of symptoms such as pain and inflammation associated with the bradykinin B1 pathway.

(I)

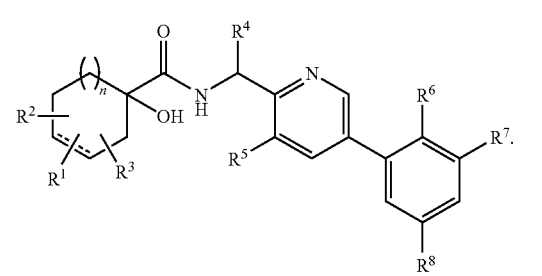

7 Claims, No Drawings

1-HYDROXYCYCLOALKANECARBOXAMIDE DERIVATIVES

CROSS REFERENCE TO RELATED APPLICATIONS

This application is a U.S. National Phase application under 35 U.S.C. §371 of PCT Application No. PCT/US2006/020668, filed May 30, 2006, which claims priority under 35 U.S.C. §119(e) from U.S. Provisional Application Ser. No. 60/687,469, filed Jun. 3, 2005.

BACKGROUND OF THE INVENTION

This invention is directed to α-hydroxyamide compounds. In particular, this invention is directed to α-hydroxyamide compounds that are bradykinin antagonists or inverse agonists.

Bradykinin ("BK") is a kinin which plays an important role in the pathophysiological processes accompanying acute and chronic pain and inflammation. Bradykinin (BK), like other kinins, is an autacoid peptide produced by the catalytic action of kallikrein enzymes on plasma and tissue precursors termed kininogens. The biological actions of BK are mediated by at least two major G-protein-coupled BK receptors termed B1 and B2. It is generally believed that B2 receptors, but not B1 receptors, are expressed in normal tissues and that inflammation, tissue damage or bacterial infection can rapidly induce B1 receptor expression. This makes the B1 receptor a particularly attractive drug target. The putative role of kinins, and specifically BK, in the management of pain and inflammation has provided the impetus for developing potent and selective BK antagonists. In recent years, this effort has been heightened with the expectation that useful therapeutic agents with analgesic and anti-inflammatory properties would provide relief from maladies mediated through a BK receptor pathway (see e.g., M. G. Bock and J. Longmore, *Current Opinion in Chem. Biol.*, 4: 401-406 (2000)). Accordingly, there is a need for novel compounds that are effective in blocking or reversing activation of bradykinin receptors. Such compounds would be useful in the management of pain and inflammation, as well as in the treatment or prevention of diseases and disorders mediated by bradykinin; further, such compounds are also useful as research tools (in vivo and in vitro).

SUMMARY OF THE INVENTION

The present invention provides α-hydroxy cycloalkanecarboxamide derivatives which are bradykinin antagonists or inverse agonists, pharmaceutical compositions containing such compounds, and methods of using them as therapeutic agents

DETAILED DESCRIPTION OF THE INVENTION

The present invention provides compounds of the formula (I) and pharmaceutically acceptable salts thereof:

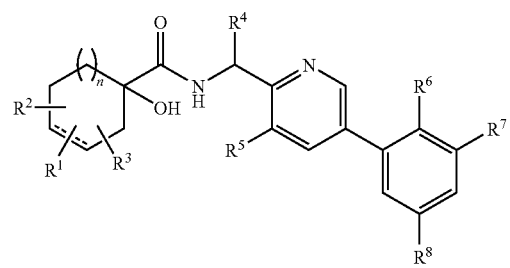

(I)

---- is a single or double bond;

$R^1$, $R^2$, and $R^3$ are each independently selected from H, halogen and OH; or $R^1$ and $R^2$ attached to the same carbon atom together represent oxo;

$R^4$ is H or methyl;

$R^5$ is Cl or F;

$R^6$ is selected from $-CO_2-C_{1-4}$alkyl, $-O-C_{1-4}$alkyl, $-O-C_{1-4}$haloalkyl, and a 5-membered heteroaromatic ring selected from triazole, oxadiazole and tetrazole wherein said heteroaromatic ring is optionally substituted with methyl, ethyl, halomethyl or haloethyl;

$R^7$ and $R^8$ are each independently Cl or F; and n is 0 or 1.

In one subset of formula (I) are compounds wherein at least one of $R^1$, $R^2$, and $R^3$ is a fluorine atom. In one embodiment thereof, $R^1$ and $R^2$ are gem-difluoro; and in one group thereof, $R^3$ is hydrogen.

In a second subset of formula (I) are compounds wherein n is 0.

In a third subset of formula (I) are compounds wherein n is 1.

In a fourth subset of formula (I) are compounds wherein $R^6$ is 1- or 2-methyltetrazol-5-yl, 1- or 2-halomethyltetrazol-5-yl, 1- or 2-haloethyltetrazol-5-yl, 5-methyl-1,2,4-oxadiazol-3-yl, 3-methyl-1,2,4-oxadiazol-5-yl, 5-halomethyl-1,2,4-oxadiazol-3-yl, 3-halomethyl-1,2,4-oxadiazol-5-yl, tetrazol-5-yl, 5-halomethyl-1,2,3-triazolyl, or 5-methyl-1,2,3-triazolyl. In one embodiment $R^6$ is 2-methyltetrazol-5-yl.

In a fifth subset of formula (I) are compounds wherein $R^4$ is methyl.

A second aspect of the present invention provides a pharmaceutical composition comprising a therapeutically effective amount of a compound of formula (I) or a pharmaceutically acceptable salt thereof, and a pharmaceutically acceptable carrier. In one subset, said pharmaceutical composition is for use in the treatment of conditions mediated by the bradykinin B1 receptor; in one embodiment thereof, said condition is pain including acute, inflammatory and neuropathic pain.

A third aspect of the present invention provides the use of a compound of formula I or a pharmaceutically acceptable salt thereof for the manufacture of a medicament for the treatment of conditions mediated by bradykinin B1 receptor. In one subset said condition is pain including acute, inflammatory and neuropathic pain.

A fourth aspect of the present invention provides a method for the treatment of a condition mediated by bradykinin B1 receptor in a mammal comprising administering to said mammal a therapeutically effective amount of a compound of formula (I) or a pharmaceutically acceptable salt thereof.

Unless otherwise stated, the following terms have the meanings indicated below:

"Alkyl" as well as other groups having the prefix "alk" such as, for example, alkoxy, alkanoyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like.

"Gem-difluoro" means two fluorine atoms attached to the same carbon atom.

"Haloalkyl" means an alkyl radical as defined above wherein at least one and up to all of the hydrogen atoms are replaced with a halogen. Examples of such haloalkyl radicals include chloromethyl, 1-bromoethyl, fluoromethyl, fluorochloromethyl, difluoromethyl, trifluoromethyl, 2,2,2-trifluoroethyl and the like. "Halomethyl" means a methyl group in which one, two or three of the hydrogen atoms are replaced with a halogen. "Haloethyl" means an ethyl group in which one, two, three, four or five of the hydrogen atoms are replaced with a halogen.

"Halogen" means fluorine, chlorine, bromine and iodine.

Optical Isomers—Diastereomers—Geometric Isomers—Tautomers.

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts thereof. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Salts.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from pharmaceutically acceptable organic non-toxic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethyl-aminoethanol, 2-dimethylaminoethanol, ethanolamine, ethylenediamine, N-ethylmorpholine, N-ethylpiperidine, glucamine, glucosamine, histidine, hydrabamine, isopropylamine, dicyclohexylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Prodrugs.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

Pharmaceutical Compositions.

Another aspect of the present invention provides pharmaceutical compositions which comprises a compound of Formula I, or a pharmaceutically acceptable salt thereof, and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 ng to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The following are examples of representative pharmaceutical dosage forms for the compounds of Formula I:

| Inj. Suspension (I.M.) | mg/mL |
|---|---|
| Cmpd of Formula I | 10 |
| Methylcellulose | 5.0 |
| Tween 80 | 0.5 |
| Benzyl alcohol | 9.0 |

| -continued | |
|---|---|
| Benzalkonium chloride | 1.0 |
| Water for injection to a total volume of 1 mL | |

| Tablet | mg/tab. |
|---|---|
| Cmpd of Formula I | 25 |
| Microcryst. Cellulose | 415 |
| Povidone | 14.0 |
| Pregelatinized Starch | 43.5 |
| Magnesium Stearate | 2.5 |
| | 500 |

| Capsule | mg/cap. |
|---|---|
| Cmpd of Formula I | 25 |
| Lactose Powder | 573.5 |
| Magnesium Stearate | 1.5 |
| | 600 |

Utilities

Compounds of this invention are antagonists or inverse agonists of bradykinin receptor, in particular the bradykinin B1 receptor, and as such are useful in the treatment and prevention of diseases and conditions mediated through the bradykinin receptor pathway such as pain and inflammation. The compounds would be effective in the treatment or prevention of pain including, for example, visceral pain (such as pancreatitis, interstitial cystitis, renal colic, prostatitis, chronic pelvic pain), neuropathic pain (such as postherpetic neuralgia, acute zoster pain, nerve injury, the "dynias", e.g., vulvodynia, phantom limb pain, root avulsions, radiculopathy, painful traumatic mononeuropathy, painful entrapment neuropathy, carpal tunnel syndrome, ulnar neuropathy, tarsal tunnel syndrome, painful diabetic neuropathy, painful polyneuropathy, trigeminal neuralgia), central pain syndromes (potentially caused by virtually any lesion at any level of the nervous system including but not limited to stroke, multiple sclerosis, spinal cord injury), and postsurgical pain syndromes (e.g., postmastectomy syndrome, postthoracotomy syndrome, stump pain)), bone and joint pain (osteoarthritis), spine pain (e.g., acute and chronic low back pain, neck pain, spinal stenosis), shoulder pain, repetitive motion pain, dental pain, sore throat, cancer pain, burn pain, myofascial pain (muscular injury, fibromyalgia), postoperative, perioperative pain and preemptive analgesia (including but not limited to general surgery, orthopedic, and gynecological), chronic pain, dysmenorrhea (primary and secondary), as well as pain associated with angina, and inflammatory pain of varied origins (e.g. osteoarthritis, rheumatoid arthritis, rheumatic disease, teno-synovitis and gout, ankylosing spondylitis, bursitis).

Further, the compounds of this invention can also be used to treat hyperreactive airways and to treat inflammatory events associated with airways disease e.g. asthma including allergic asthma (atopic or non-atopic) as well as exercise-induced bronchoconstriction, occupational asthma, viral- or bacterial exacerbation of asthma, other non-allergic asthmas and "wheezy-infant syndrome". Compounds of the present invention may also be used to treat chronic obstructive pulmonary disease including emphysema, adult respiratory distress syndrome, bronchitis, pneumonia, allergic rhinitis (seasonal and perennial), and vasomotor rhinitis. They may also be effective against pneumoconiosis, including aluminosis, anthracosis, asbestosis, chalicosis, ptilosis, siderosis, silicosis, tabacosis and byssinosis.

Compounds of the present invention may also be used for the treatment of inflammatory bowel disease including Crohn's disease and ulcerative colitis, irritable bowel syndrome, pancreatitis, nephritis, cystitis (interstitial cystitis), uveitis, inflammatory skin disorders such as psoriasis and eczema, rheumatoid arthritis and edema resulting from trauma associated with burns, sprains or fracture, cerebral edema and angioedema (including hereditary angioedema and drug-induced angioedema such as that caused by angiotensin converting enzyme (ACE) or ACE/neutral endopeptidase inhibitors, e.g. omepatrilat). They may be used to treat diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion). They may be used as smooth muscle relaxants for the treatment of spasm of the gastrointestinal tract or uterus. Additionally, they may be effective against liver disease, multiple sclerosis, cardiovascular disease, e.g. atherosclerosis, congestive heart failure, myocardial infarct; neurodegenerative diseases, eg. Parkinson's and Aizheimers disease, epilepsy, septic shock e.g. as anti-hypovolemic and/or anti-hypotensive agents, headache including cluster headache, migraine including prophylactic and acute use, stroke, closed head trauma, cancer, sepsis, gingivitis, osteoporosis, benign prostatic hyperplasia and hyperactive bladder. Animal models of these diseases and conditions are generally well known in the art, and may be suitable for evaluating compounds of the present invention for their potential utilities. Finally, compounds of the present invention are also useful as research tools (in vivo and in vitro).

The compounds of this invention are useful in the treatment of pain and inflammation by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

The compounds would be effective in the treatment or prevention of pain including, for example, bone and joint pain (osteoarthritis), repetitive motion pain, dental pain, cancer pain, myofascial pain (muscular injury, fibromyalgia), perioperative pain (general surgery, oral surgery, gynecological), neuropathic pain (postherpetic neuralgia), and chronic pain by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

In particular, inflammatory pain such as, for example, inflammatory airways disease (chronic obstructive pulmonary disease) would be effectively treated by the compounds of this invention by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Further, the compounds of this invention can additionally be used to treat asthma, inflammatory bowel disease, rhinitis, pancreatitis, cystitis (interstitial cystitis), uveitis, inflammatory skin disorders, rheumatoid arthritis and edema resulting from trauma associated with burns, sprains or fracture by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used subsequent to surgical intervention (e.g. as post-operative analgesics) and to treat inflammatory pain of varied origins (e.g. osteoarthritis, rheumatoid arthritis, rheumatic disease, teno-synovitis and gout) as well as for the treatment of pain associated with angina, menstruation or cancer by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat diabetic vasculopathy, post capillary resistance or diabetic symptoms associated with insulitis (e.g. hyperglycemia, diuresis, proteinuria and increased nitrite and kallikrein urinary excretion) by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat inflammatory skin disorders such as psoriasis and eczema by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used as smooth muscle relaxants for the treatment of spasm of the gastrointestinal tract or uterus or in the therapy of Crohn's disease, ulcerative colitis or pancreatitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Such compounds may be used therapeutically to heat hyperreactive airways and to treat inflammatory events associated with airways disease e.g. asthma, and to control, restrict or reverse airways hyperreactivity in asthma by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may be used to treat intrinsic and extrinsic asthma including allergic asthma (atopic or non-atopic) as well as exercise-induced bronchoconstriction, occupational asthma, viral or bacterial exacerbated asthma, other non-allergic asthmas and "wheezy-infant syndrome" by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

They may also be effective against pneumoconiosis, including aluminosis, anthracosis, asbestosis, chalicosis, ptilosis, siderosis, silicosis, tabacosis and byssinosis was well as adult respiratory distress syndrome, chronic obstructive pulmonary or airways disease, bronchitis, allergic rhinitis, and vasomotor rhinitis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Additionally, they may be effective against liver disease, multiple sclerosis, atherosclerosis, Alzheimer's disease, septic shock e.g. as anti-hypovolemic and/or anti-hypotensive agents, cerebral edema, headache including cluster headache, migraine including prophylactic and acute use, closed head trauma, irritable bowel syndrome and nephritis by the administration of a tablet, cachet, or capsule each containing, for example, 0.1 mg, 0.5 mg, 1 mg, 3 mg, 5 mg, 10 mg, 25 mg, 50 mg, 100 mg, 125 mg, 250 mg, or 500 mg of a compound of this invention once every three to four hours, once, twice or three times a day, or (in an extended release formulation) once, twice or three times a week.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I, either administered separately or in the same pharmaceutical compositions, include, but are not limited to: (1) morphine and other opiate receptor agonists including codeine, oxycodone, propoxyphene (Darvon) and tramadol; (2) non-steroidal antiinflammatory drugs (NSAIDs) including COX-2 inhibitors such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib); (3) corticosteroids such as betamethasone, budesonide, cortisone, dexamethasone, hydrocortisone, methylprednisolone, prednisolone, prednisone and triamcinolone; (4) histamine H1 receptor antagonists such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, desloratadine, fexofenadine and levocetirizine; (5) histamine H2 receptor antagonists such as cimetidine, famotidine and ranitidine; (6) proton pump inhibitors such as omeprazole, pantoprazole and esomeprazole; (7) leukotriene antagonists and 5-lipoxygenase inhibitors such as zafirlukast, montelukast, pranlukast and zileuton; (8) drugs used for angina, myocardial ischemia including nitrates such as nitroglycerin and isosorbide nitrates, beta blockers such as atenolol, metoprolol, propranolol, acebutolol, betaxolol, bisoprolol, carteolol, labetalol, nadolol, oxprenolol, penbutolol, pindolol, sotalol and timolol, and calcium channel blockers such as diltiazam, verapamil, nifedipine, bepridil, felodipine, flunarizine, isradipine, nicardipine and nimodipine; (9) incontinence medications such as antimuscarinics, e.g., tolterodine and oxybutinin); (10) gastrointestinal antispasmodics (such as atropine, scopolamine, dicyclomine, antimuscarinics, as well as diphenoxylate); skeletal muscle relaxants (cyclobenzaprine, carisoprodol, chlorphenesin, chlorzoxazone, metaxalone, methocarbamol, baclofen, dantrolene, diazepam, or orphenadrine); (11) gout medications such as allopurinol, probenicid and colchicine; (12) drugs for rheumatoid arthritis such as methotrexate, auranofin, aurothioglucose and gold sodium thiomalate; (13) drugs for osteoporosis such as alendronate and raloxifene; (14) decongestants such as pseudoephedrine and phenylpropanolamine; (15) local anesthetics; (16) anti-herpes drugs such as acyclovir, valacyclovir and famcyclovir; (17) anti-emetics such as ondansetron and granisetron; (18) migraine drugs such as the triptans (e.g. rizatriptan, sumatriptan), ergotamine, dihydroergotamine, CGRP antagonists, (19) antidepressants (e.g., tricyclic antidepressants (such as doxepin, clomipramine, imipramine, amitriptyline, maprotiline, nortriptyline), serotonin-selective/serotonin and norepinephrine reuptake inhibitors (such as paroxetine, fluoxetine, duloxetine, vanlafexine), beta-adrenergic blockers; (20) VR1 antagonsits; (21) anticonvulsants (e.g., gabapentin, pregabalin, lamotrigine, topiramate, carbamazepine, oxcarbazepine, phenyloin); (22) glutamate antagonists (e.g., ketamine and other NMDA antagonists, NR2B antagonists); (23) acetaminophen; (24) CCR2 antagonists; (25) PDE4 antagonists such as roflumilast; (26) tegaserod; (27) alosetron; (28) topiramate; (29) cathepsin K inhibitors; (30) ACE inhibitors such as enalapril and lisinopril; and (31) ACE/NEP inhibitors such as omepatrilat.

Biological Evaluation.

(a) Assessing the Affinity of Selected Compounds to Bind to the Bradykinin B1 or B2 Receptor.

Radioligand binding assays are performed using membranes from CHO cells that stably express the human, rabbit, rat, or dog B1 receptors or CHO cells that express the human B2 receptor. For all receptor types, cells are harvested from culture flasks in PBS/1 mM EDTA and centrifuged at 1000×g for 10 minutes. The cell pellets are homogenized with a polytron in ice cold 20 mM HEPES, 1 mM EDTA, pH 7.4 (lysis buffer) and centrifuged at 20,000×g for 20 minutes. The membrane pellets are rehomogenized in lysis buffer, centrifuged again at 20,000×g and the final pellets are resuspended at 5 mg protein/ml in assay buffer (120 mM NaCl, 5 mM KCl, 20 mM HEPES, pH 7.4) supplemented with 1% BSA and frozen at −80° C.

On the day of assay, membranes are centrifuged at 14,000×g for 5 minutes and resuspended to the desired protein concentration in assay buffer containing 100 nM enaliprilat, 140 μg/mL bacitracin and 0.1% BSA. 3H-des-arg10, leu9 kallidin is the radioligand used for the human and rabbit B1 receptors, 3H-des-arg10 kallidin is used for the rat and dog B1 receptors, and 3H-bradykinin is used to label the human B2 receptor.

For all assays, compounds are diluted from DMSO stock solutions with 4 μL added to assay tubes for a final DMSO concentration of 2%. This is followed by the addition of 100 μL radioligand and 100 μL of the membrane suspension. Nonspecific binding for the B1 receptor binding assays is determined using 1 μM des-arg10 kallidin and nonspecific binding for the B2 receptor is determined with 1 μM bradykinin. Tubes are incubated at room temperature (22° C.) for 60 minutes followed by filtration using a Tomtec 96-well harvesting system. Radioactivity retained by the filter is counted using a Wallac Beta-plate scintillation counter.

The compounds of this invention have affinity for the B1 receptor in the above assay as demonstrated by results of less than 5 μM. It is advantageous that the assay results be less than 1 μM, even more advantageous for the results be less than 0.5 μM. It is further advantageous that compounds of this invention have affinity for the bradykinin B1 receptor over the bradykinin B2 receptor; more advantageously, the affinity for the B1 receptor is at least 10 fold, and preferably over 100 fold, over that for the B2 receptor.

(b) Assay for Bradykinin B1 Antagonists.

B1 agonist-induced calcium mobilization was monitored using a Fluorescence Imaging Plate Reader (FLIPR). CHO cells expressing the B1 receptor were plated in 96 or 384 well plates and allowed to incubate in Iscove's modified DMEM overnight. Wells were washed two times with a physiological buffered salt solution and then incubated with 4 uM Fluo-3 for one hour at 37° C. The plates were then washed two times with buffered salt solution and 100 uL of buffer was added to each well. Plates were placed in the FLIPR unit and allowed to equilibrate for two minutes. The test compound was then added in 50 ul volumes followed five minutes later by 50 ul of agonist (des-arg$^{10}$ kallidin). Relative fluorescence peak heights in the absence and presence of antagonist were used to calculate the degree of inhibition of the B1 receptor agonist response by the test compound. Eight to ten concentrations of test compound were typically evaluated to construct an inhibition curve and determine IC$_{50}$ values using a four-parameter nonlinear regression curve fitting routine.

(c) Assay for Bradykinin Inverse Agonists.

Inverse agonist activity at the human B1 receptor was evaluated using transiently transfected HEK293 cells. One day following transfection cell flasks were labeled overnight with 6 uCi/ml [$^3$H]myo-inositol. On the day of assay, the media was removed and the attached cells were gently rinsed with 2×20 ml of phosphate-buffered saline. Assay buffer (HEPES buffered physiological salts, pH 7.4) was added and the cells were detached by tapping of the flask. The cells were centrifuged at 800×g for five minutes and resuspended at 1×10$^6$ cells/ml in assay buffer supplemented with 10 mM lithium chloride. After 10 minutes at room temperature, one-half ml aliquots were distributed to tubes containing test compound or vehicle. After an additional 10 minutes the tubes were transferred to a 37° C. water bath for 30 minutes. The incubation was terminated by the addition of a 12% perchloric acid solution and the tubes were placed on ice for 30 minutes. The acid was then neutralized with KOH and the tubes centrifuged to pellet precipitated material. [$^3$H]Inositol monophosphate formed was recovered by standard ion exchange chromatographic techniques and quantitated by liquid scintillation counting. Inverse agonist activity was determined by the degree to which a test compound reduced basal (cells incubated with vehicle) levels of [³H]inositol monophosphate accumulation.

Abbreviations Used.

The following abbreviations have the meanings indicated, unless stated otherwise in the specification: Ac=aceryl; Boc=t-butoxycarbonyl; Cat=catalyst; DCM=dichloromethane; DMADMA=dimethylacetamide dimethyl acetal; DMF=dimethylformamide; DMSO=dimethyl sulfoxide; EDCI=1-(3-dimethylaminopropyl)-3-ethylcarbodiimide; Et=ethyl; EtOAc=ethyl acetate; HOBT=1-hydroxybenzo-triazole; KHMDS=potassium hexamethyldisilazane; LAH=lithium aluminum hydride; LDA=lithium diisopropylamide; Me=methyl; NBS=N-bromosuccinimide; NMO=N-methylmorpholino N-oxide; Ph=phenyl; Rt=room temperature; TBAF=tetrabutylammonium fluoride; TEA=triethylamine; Tf=triflyl (trifluoromethanesulfonyl); TFAA=trifluoroacetic anhydride; THF=tetrahydrofuran.

Methods of Synthesis

Compounds of formula I may be prepared by the general procedure depicted in Scheme 1. The α-hydroxycarboxylic acid (1) is coupled with the biarylamine (2) using standard reagents and reaction conditions for amide bond formation, such as EDCI/HOBt.

derivative (6) using a Suzuki reaction in the presence of a triarylphosphine, like triphenylphosphine, and a metal catalyst, like palladium acetate. The resultant Boc protected biphenyl intermediate is deprotected with an acid such as HCl in an appropriate solvent to provide the biaryl amine derivative (2).

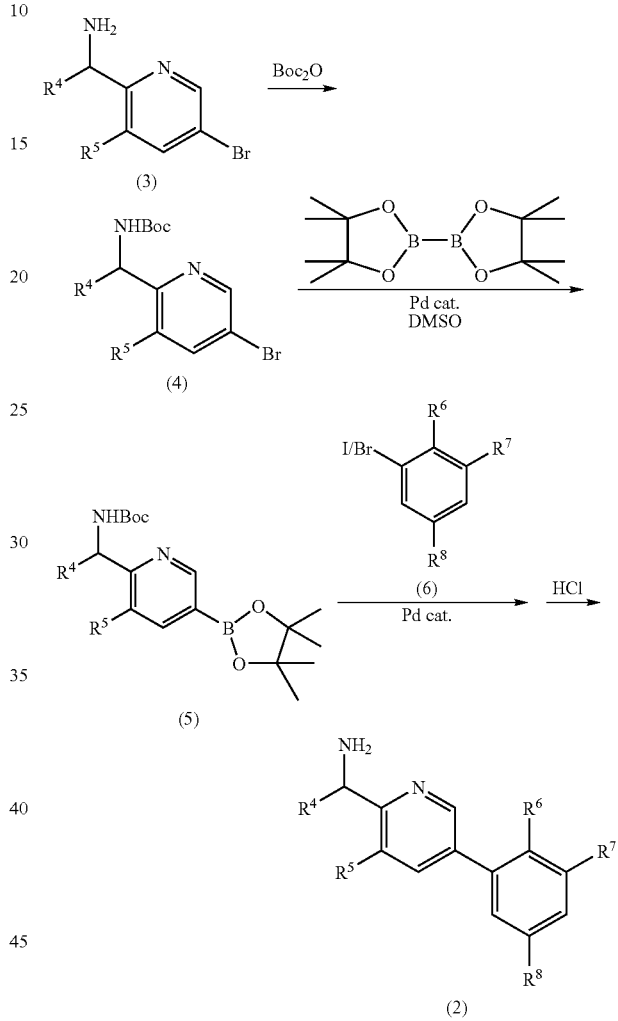

The preparation of the hydroxy acids using conventional chemical reactions well known in the art is shown in Schemes 3 and 4. In Scheme 3, the appropriate ketone is converted to the cyanohydrin using a reagent such as potassium cyanide. The intermediate cyanohydrin is hydrolyzed using strong acid such as concentrated HCl to afford the hydroxy acid (1).

The carboxylic acids (1) are commercially available or may be prepared from commercially available reagents using conventional chemical reactions well known in the art (Schemes 3 and 4). The amines (2) may be prepared as outlined in Scheme 2.

As illustrated in Scheme 2, the synthesis begins with amines such as (3) which may be prepared from commercially available reagents using conventional chemical reactions well known in the art. Amine derivative (4), after primary amine protection with an appropriate protecting group, like Boc, is elaborated to the pinacol boron ester (5) using a palladium catalyst in an appropriate solvent, like dimethyl sulfoxide. This boron ester (5) is coupled to an aryl halide

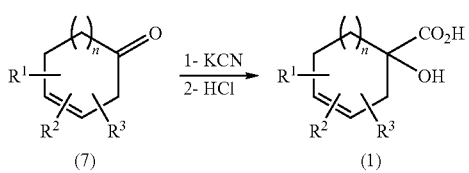

Alternatively, the hydroxy acid (1) may be prepared from the appropriated ester, such as a benzyl ester (8) as shown in Scheme 4. Formation of the enolate using a base such as potassium hexamethyldisilazane in the appropriate solvent such as THF is followed by reaction with a hydroxyl transfer reagent such as Davis's reagent (9). Removal of the benzyl ester may be carried out via hydrogenolysis with a metal catalyst such as palladium to afford the hydroxy acid (1).

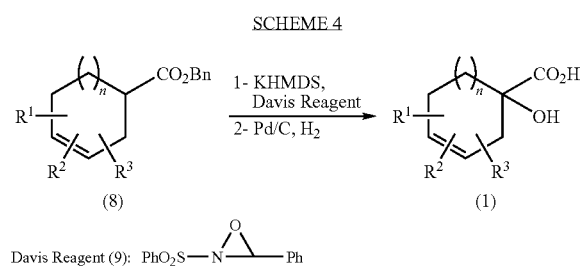

Preparation of the amines (3) is shown in Scheme 5. Reduction of the nitro group and nitrile hydrolysis of known pyridine (10) (*J. Chem. Soc.* (1952), 2042-2046) is followed by conversion of the resultant amine to the chloride to afford (11). The amide is converted in a 3 step sequence to aldehyde (12). Imine formation with t-butyl sulfinamide is followed by addition of methyl Grignard and subsequent hydrolysis to produce (3a), which may be further elaborated to provide the biarylmethanamine as shown above. Alternatively, amide (11) may be converted to the nitrile with TFAA followed by reduction with a reagent such as Dibal to produce amine (3b).

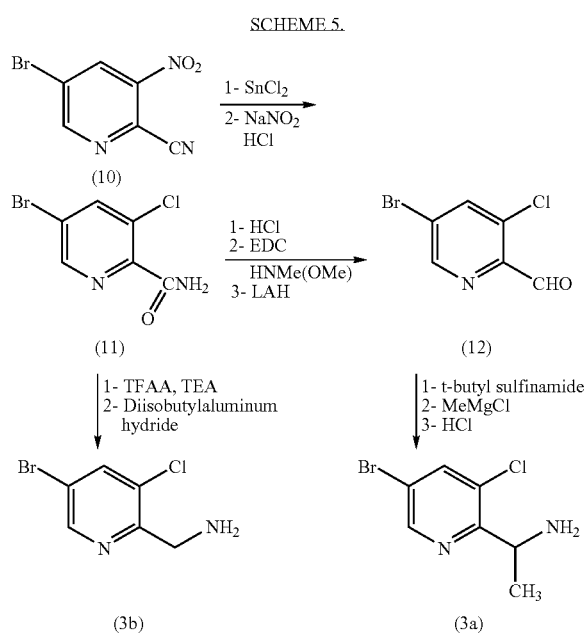

Alternatively, the amines (3) may be prepared as shown in Scheme 6. Displacement of the nitro group of (10) using a fluoride source such as tetrabutylammonium fluoride in a solvent like DMF affords (13). Reduction with a metal hydride such as Dibal affords amine (3d). Addition of MeMgCl to nitrile (13), quenching with acetic anhydride, and asymmetric reduction of the resulting enamide with a catalyst such as Rhodium affords (14). Removal of the acetamide with HCl in MeOH affords amine (3c).

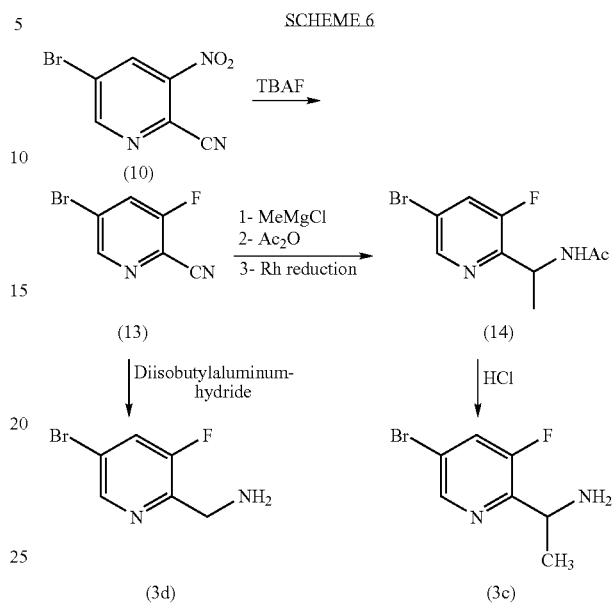

The following examples are provided to illustrate the preparation of the biarylmethylamine starting materials. Other biarylmethylamines may be similarly prepared.

REFERENCE EXAMPLES

1.
N-[1-(5-Bromo-3-fluoropyridin-2-yl)vinyl]acetamide

Step 1. 2,5-Dibromo-3-nitropyridine. 2-Hydroxy-3-nitro-5-bromopyridine (1 eq) was suspended in toluene (3 vol) and N,N-dimethylformamide (0.1 eq) was added. The mixture was protected from light. A solution of phosphorus oxybromide (1.2 eq) in toluene (2 vol) was added to the pyridine mixture over 1.5 h at about 90° C. and the reaction was aged for about 14 h at 90° C. The reaction mixture was cooled to room temperature and water (10 vol) and toluene (5 vol) were added. The layers were cut and the organic layer was washed with 1N NaOH (2×10 vol) and H$_2$O (5 vol). The batch was concentrated under reduced pressure to yield the desired product.

Step 2. 5-Bromo-3-nitropyridine-2-carbonitrile. The compound of Step 1 (1 eq) was suspended in propionitrile (3 vol). Copper cyanide (1.1 eq) was added and the mixture was heated to 90° C. and aged for about 17 h. The reaction mixture was cooled to room temperature and isopropyl acetate (12 vol) and saturated brine (8 vol) were added. The mixture was stirred for 15 min and the layers were cut. The top organic layer was washed with brine (4×6 vol). The batch concentrated under reduced pressure to yield the desired product.

Step 3. 5-Bromo-3-fluoropyridine-2-carbonitrile. Sulfuric acid (0.02 eq) was added to a solution of tetrabutylammonium fluoride (3 eq) in DMF (5 vol) and the mixture cooled to −40° C. A solution of the compound of Step 2 (1 eq) in DMF (2 vol) was added maintaining die temperature <−35° C. After about 20 minutes 2N HCl (3 vol) was added followed by 1N HCl (15 vol). The precipitated product was collected by filtration to give the desired product.

Step 4. N-[1-(5-Bromo-3-fluoropyridin-2-yl)vinyl]acetamide. Compound of Step 3 (1 eq) was dissolved in toluene (10 vol). The batch was cooled to −10° C. and MeMgCl (1.5 eq) was added maintaining the temperature <0° C. The mixture was aged for 1 h and acetic anhydride was added over approximately 30 min maintaining the temperature <0° C. The reaction was aged for 18 h at −10° C. The mixture was quenched with half-saturated NaHCO$_3$ (6 vol) and aged at 20-25° C. for 30 min. The layers were separated and the organic layer was washed with water (5 vol), 10% aqueous Na$_2$SO$_4$ (2×5 vol) and water (2×5 vol). The batch was concentrated under vacuum to give the title compound.

2. N-[(1R)-1-(5-Bromo-3-fluoropyridin-2-yl)ethyl] acetamide

In a nitrogen filled glovebox (<10 ppm O$_2$), (S,S,R,R)-Tangphos (1.05 equivalents relative to Rh) was combined with (COD)$_2$RhBF$_4$ and dissolved in methanol to make a solution that was 0.107M in Rh. The catalyst solution was aged for 1 h.

In an nitrogen filled glovebox the catalyst solution (((S,S,R,R)-Tangphos)Rh(COD)BF$_4$, 0.00284 eq, S/C=352) was transferred to a stainless steel cylinder (see figure) along with methanol rinse (1 volume). To a separate stainless steel cylinder an additional charge of methanol (1 volume) was added. These two cylinders were connected via a ball-valve.

The enamide of Reference Example 1 (54 wt % in MeOH) was drawn into a stirred autoclave via vacuum followed by a methanol (10 mL/g enamide) rinse. The solution was then degassed with nitrogen (3×). The stainless steel vessels containing the catalyst solution were connected to the autoclave via flexible tubing. The autoclave was placed under partial vacuum and the catalyst solution was drawn into the autoclave followed by the MeOH rinse. The solution was degassed with H$_2$ (100 psig) 3× and the final pressure adjusted to 20 psig. The reaction temperature was set to 25° C. and agitation initiated. The reaction pressure was increased to 98 psig after 20 minutes. The mixture was hydrogenated for an additional 4 h. Enantiomeric excess was 99.5%.

The batch was removed from the autoclave and concentrated under vacuum and solvent switched to isopropyl acetate (IPAc) to a final concentration of 10 mL/g. The IPAc solution was filtered through silica gel (300 wt %), and washed with 1 volume of IPAc. Darko KB-B (50 wt %) was added and the mixture aged for 16 h at 20-25° C. The batch was filtered through Solka Floe and the cake washed with IPAc (1.1 volumes). The batch was concentrated under vacuum to give the title compound.

3. 5-(2-Bromo-4-chloro-6-fluorophenyl)-2-methyl-2H-tetrazole

A solution of 2-brorao-4-chloro-6-fluorobenzonitrile (16.8 g, 71.4 mmol) and azidotrimethyltin (15.4 g, 75.0 mmol) in 70 mL toluene was heated to 120° C. for 72 hours. The solution was cooled to room temperature and partitioned between ethyl acetate and 0.5 N HCl. The organic extract was washed with water and brine, dried over Na$_2$SC$_4$, filtered and concentrated under vacuum to provide 5-(2-bromo-4-chloro-6-fluorophenyl)-1H-tetrazole that gave proton NMR spectra consistent with theory and a mass ion (ES+) of 278.9 for M+H+.

A mixture of the above tetrazole (16.0 g, 57.7 mmol), potassium carbonate (12.0 g, 86.5 mol), and iodomethane (11.5 g, 80.7 mol) in 15 mL DMF was stirred at room temperature for 3 hours. The mixture was partitioned between ethyl acetate and water, and the organic extract was washed with water and brine, dried over Na$_2$SO$_4$, filtered and concentrated under vacuum. The residue was subjected to silica gel chromatography eluted with 0-10% ethyl acetate in hexanes to provide the title compound that gave proton NMR spectra consistent with theory and a mass ion (ES$^+$) of 293.0 for M+H$^+$.

4. ((1R)-1-{5-[5-chloro-3-fluoro-2-(2-methyl-2H-tetrazol-5-yl)phenyl]-3-fluoropyridin-2-yl}ethyl) amine A solution of N-[(1R)-1-(5-bromo-3-fluoropyridin-2-yl) ethyl]acetamide (30.4 g, 116.6 mmol,) in 30 mL of anhydrous MeOH was saturated with anhydrous HCl. After sealing the reaction vessel, the solution was heated to 60° C. for 16 hours. After cooling to ambient temperature, solvent was removed under reduced pressure to obtain a brownish tan solid. This solid was dissolved in 100 mL of dichloromethane and the resulting solution was cooled to 0° C. in an ice bath. To this cooled solution was added 31.4 mL of triethylamine (225.2 mmol). A solution of Boc-anhydride (33.5 g, 153.5 mmol) in 25 mL of dichloromethane was then added and the reaction was allowed to warm to room temperature. After stirring for 16 hours, the volume of dichloromethane was reduced in vacuo and the resulting residue was taken up in EtOAc. The organic solution was washed with 1N NaOH, dried over sodium sulfate, filtered and concentrated to a crude oil, which was subjected to chromatography on silica gel eluting with 0-5% EtOAc in hexanes to yield tert-butyl[(1R)-1-(5-bromo-3-fluoropyridin-2-yl)ethyl]-carbamate.

A mixture of potassium acetate (2.92 g, 29.8 mmol), the above carbamate (3.17 g, 9.9 mmol) and 4,4,4',4',5,5,5',5'-octamethyl-2,2'-bi-1,3,2-dioxaborolane (2.77 g, 10.9 mmol) was dissolved in 10 mL of DMSO in a sealed tube reaction vessel caped with a rubber septum. This heterogeneous mixture was then evacuated and purged with nitrogen three times prior to introduction of [1,1'-bis-(diphenylphosphino)ferrocene]dichloro-palladium(II), complex with DCM (1:1) (0.363 g, 0.500 mmol). The heterogeneous mixture was then evacuated and purged with nitrogen twice before the septum was replaced with a teflon screw-top cap. This sealed vessel was then heated to 90° C. for 16 hours. After cooling to ambient temperature, potassium carbonate (2.74 g, 19.9 mmol), water (9.9 mL), 5-(2-bromo-4-chloro-6-fluorophenyl)-2-methyl-2H-tetrazole (3.04 g, 10.4 mmol) and additional palladium catalyst (0.363 g, 0.500 mmol) were added and the reaction vessel was sealed again. After heating to 80° C. for 5 hours, the reaction was cooled and then quenched with water. The mixture was flushed through a plug of celite and chased with EtOAc. The aqueous layer was extracted once with EtOAc. The combined organic layers were washed with water and brine prior and dried over sodium sulfate. Filtration and solvent removal provided material which was subjected to silica gel chromatography eluting with 0-10% EtOAc in hexanes to yield tert-butyl((1R)-1-{5-[5-chloro-3-fluoro-2-(2-methyl-2H-tetrazol-5-yl)phenyl]-3-fluoropyridin-2-yl}ethyl)carbamate. This material was dissolved in 15 mL of dry EtOAc. Anhydrous HCl gas was then bubbled through the solution for 3 minutes. The reaction was stirred vigorously for one hour. The reaction mixture was slowly neutralized with a saturated aqueous sodium bicarbonate solution. The mixture was partitioned between water and EtOAc. The organic layer was washed with water and brine and dried over sodium sulfate. Filtration and concentration provided the title compound as an oil.

5. 3-(2-Bromo-4-chloro-6-fluorophenyl)-5-methyl-1,2,4-oxadiazole

A solution of 2-bromo-4-chloro-6-fluoroaniline (25.0 g, 111 mmol) in 200 mL of anhydrous DCM, in a 2 liter round-bottom flask equipped with a bubbler, was treated with nitrosonium tetrafluoroborate (14.3 g, 123 mmol), at ambient temperature. After 1 hour complete consumption of the aniline was observed. The reaction mixture was cooled to 0° C. prior to the addition of potassium cyanide (14.5 g, 223 mmol). With rapid stirring, an aqueous solution of cupric sulfate hexahydrate (55.6 g, 223 mmol in 125 mL of water) was slowly added producing a large volume of gas evolution. After stirring for 40 minutes, the ice bath was removed and the reaction was allowed to warm to ambient temperature. After 1 hour at ambient temperature, the reaction mixture was diluted with additional DCM and then slowly quenched by the addition of aqueous saturated sodium bicarbonate until additional gas evolution is no longer observed. The resulting heterogeneous mixture was then filtered through a large pad of celite, washing with DCM as needed. The organic filtrate was then washed twice with saturated brine prior to drying over sodium sulfate. Filtration and solvent removal provided material which was subjected to silica gel chromatography eluting with 0-25% DCM in heptane. Collection of product containing fractions and removal of solvent yielded 9.76 grams of 2-bromo-4-chloro-6-fluorobenzo-nitrile, which gave LC/MS and proton NMR spectra consistent with theory.

To 21 mL of ethanol was added the above nitrile (5.00 g, 21.3 mmol) followed by excess hydroxylamine (21 mL of a 50% aqueous hydroxylamine solution). This mixture was then headed to 60° C. while open to the atmosphere. After 1.5 hours the reaction was judged complete by LC/MS analysis. The mixture was allowed to cool to ambient temperature before being diluted with diethyl ether and water. The ethereal layer was washed with additional water, then twice with saturated brine. The organic layer was dried over sodium sulfate, filtered and then concentrated to obtain 5.5 g of unpurified hydroxylamine adduct. This material was combined with an equivalent quantity of unpurified hydroxyl-amine adduct prepared in parallel to give a total mass of ~11.1 grams. This 11.1 grams of material was dissolved in DMADMA (38.7 g, 290. mmol) and allowed to stir at ambient temperature for 30 minutes. The reaction mixture was then diluted with diethyl ether and washed with water, half-saturated brine and then brine prior to drying over sodium sulfate. Filtration and solvent removal provided material which was subjected to silica gel chromatography eluting with 40-85% DCM in hexanes. Collection of product containing fractions and removal of solvent yielded 5.08 grams of the title compound, which gave LC/MS and proton NMR spectra consistent with theory.

The following examples are provided to illustrate the invention and are not to be construed as limiting the scope of the invention in any manner.

Example 1

N-({5-[5-chloro-3-fluoro-2-(2-methyl-2/f-tetrazol-5-yl)phenyl]-3-fluoropyridin-2-yl}methyl)-1-hydroxy-cyclopentanecarboxamide

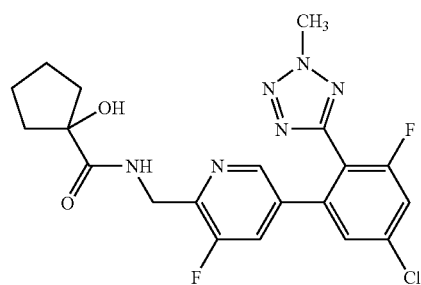

A mixture of cyclopentanone (20.0 g, 237.8 mmol), potassium cyanide (18.6 g, 285.3 mmol) and 34 mL of deionized water was stirred vigorously. In a separate flask, sodium bisulfite (29.7 g, 285.3 mmol) was dissolved in 36 mL of deionized water. An addition funnel was attached to the reaction flask and then filled with the sodium bisulfite solution. To the stirring reaction mixture was added the sodium bisulfite solution, dropwise over 15 minutes. The reaction mixture was allowed to stir vigorously for 16 hours. The biphasic reaction mixture was partitioned between the water and EtOAc. The aqueous layer was extracted three times with EtOAc. The combined organic layers were dried over sodium sulfate, filtered and concentrated to provide 1-hydroxycyclopentanecarbonitrile.

The 1-hydroxycyclopentanecarbonitrile (29.9 g, 268.8 mmol) was heated to reflux in 56 mL of concentrated hydrochloric acid for 16 hours. The volume of concentrated hydrochloric acid was reduced in vacuo and the resulting residue was taken up in chloroform. The resulting slurry was filtered and washed with additional chloroform. The organic washings were combined, dried over sodium sulfate and concentrated to yield 1-hydroxycyclopentanecarboxylic acid.

A mixture of potassium acetate (3.10 g, 31.6 mmol), tert-butyl[(5-bromo-3-fluoropyridin-2-yl)methyl]carbamate (3.21 g, 10.5 mmol) and 4,4,4',4',5,5,5',5'-octamethyl-2,2'-bi-1,3,2-dioxaborolane (2.94 g, 11.6 mmol) in a sealed tube reaction vessel capped with a rubber septum was dissolved in 10 mL of DMSO. This heterogeneous mixture was then evacuated and purged with nitrogen three times prior to introduction of [1,1'-bis(diphenylphosphino)ferrocene]dichloropalladium(II), complex with DCM (1:1) (0.385 g, 0.530 mmol). The heterogeneous mixture was then evacuated and purged with nitrogen twice before the septum was replaced with a teflon screw-top cap. This sealed vessel was then heated to 90° C. for 2 hours. After cooling to ambient temperature, potassium carbonate (2.91 g, 21.1 mmol), water (10.5 mL), 5-(2-bromo-4-chloro-6-fluorophenyl)-2-methyl-2H-tetrazole (3.38 g, 11.6 mmol) and additional palladium catalyst (0.385 g, 0.530 mmol) were added and the reaction was sealed again. After heating to 80° C. for 1 hour, the reaction was cooled, quenched with water, and partitioned between EtOAc and water. The mixture was filtered through a plug of celite with EtOAc. The aqueous layer was extracted once with EtOAc. The combined organic layers were washed with additional water and then brine prior to drying over sodium sulfate. Filtration and solvent removal provided material which was subjected to chromatography on silica gel eluting with 0-15% EtOAc in hexanes to yield tert-butyl({5-[5-chloro-3-fluoro-2-(2-methyl-2H-tetrazol-5-yl)phenyl]-3-fluoropyridin-2-yl}methyl)carbamate.

The above carbamate was dissolved in 50 mL of dry EtOAc. Anhydrous HCl gas was then bubbled through the solution for 3 minutes. The reaction was stirred vigorously for one hour. The reaction mixture was slowly neutralized with a saturated aqueous sodium bicarbonate solution. The mixture was partitioned between water and EtOAc. The organic layer was washed with water and brine prior to drying over sodium sulfate. The extracts were filtered, concentrated, and purified by chromatography on silica gel eluting with 0-20% MeOH in dichloromethane to provide ({5-[5-chloro-3-fluoro-2-(2-methyl-2H-tetrazol-5-yl)phenyl]-3-fluoropyridin-2-yl}methyl)amine.

To a mixture of the above fluoropyridinium compound (1.02 g, 2.48 mmol), 1-hydroxy-cyclopentanecarboxylic acid (0.485 g, 3.72 mmol), (1H-1,2,3-benzotriazol-1-yloxy)[his(dimethyl-amino)]phosphonium hexafluorophosphate (1.76 g, 3.97 mmol) in anhydrous dichloromethane (16 mL) was added triethylamine (0.754 g, 7.45 mmol). The reaction mixture was allowed to stir at ambient temperature for 1 hour. After the reaction was judged complete by LC/MS analysis, the volume of the reaction is reduced in vacuo. The residue was taken up in EtOAc, and the organic phase was successively washed with water, 0.25 N HCl and saturated sodium bicarbonate solution. The combined extracts were dried over sodium sulfate, filtered, and concentrated. The crude material was subjected to chromatography on silica gel eluting with 0-50% EtOAc in hexanes to yield the title compound as a white solid; which gave a proton NMR spectrum consistent with theory and a mass ion (ES+) of 449.2 for M+H+: $^1$H NMR (500 MHz, CDCl$_3$) δ 8.13 (s, 1H), 7.87 (bs, NH), 7.34 (d, J=8.8 Hz, 1H), 7.26 (m, 2H), 4.65 (d, J=4.8 Hz, 2H), 4.35 (s, 3H), 2.23-2.21 (m, 3H), 1.85-1.84 (m, 4H), 1.77-1.74 (m, 2H).

The following compounds were prepared according to the general procedure provided in Example 1. The starting materials are either commercially available or may be prepared from commercially available reagents using conventional reactions well known in the art.

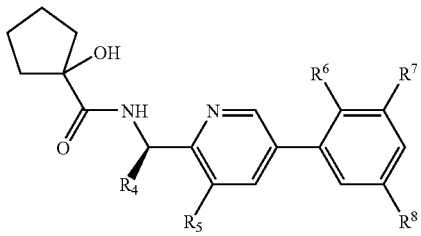

| Ex. | R⁴ | R⁶ | R⁵ | R⁷ | R⁸ | LRMS (M + H⁺) |
|---|---|---|---|---|---|---|
| 2 | Me | 5-CH₂F-1,2,4-oxadiazole | F | F | Cl | 480 |
| 3 | Me | CO₂CH₃ | F | Cl | Cl | 455 |
| 4 | Me | 3-CH₃-1,2,4-oxadiazole | F | Cl | Cl | 479 |
| 5 | Me | 3-CH₃-1,2,4-oxadiazole | F | Cl | F | 461 |
| 6 | Me | 2-CH₃-2H-tetrazol-5-yl | F | F | Cl | 461 |
| 7 | Me | 2-CH₃-2H-tetrazol-5-yl | F | F | F | 447 |
| 8 | Me | 5-CH₃-1,2,4-oxadiazole | Cl | F | Cl | 479 |
| 9 | Me | 5-CH₃-1,2,4-oxadiazole | F | Cl | Cl | 479 |
| 10 | Me | 3-CH₃-1,2,4-oxadiazole | F | F | Cl | 461 |
| 11 | Me | 2-CH₃-2H-tetrazol-5-yl | Cl | Cl | Cl | 493 |
| 12 | Me | 2-CH₃-2H-tetrazol-5-yl | F | Cl | Cl | 479 |
| 13 | Me | OCH₂CH₃ | F | Cl | Cl | 441 |
| 14 | Me | 2-CH₃-2H-tetrazol-5-yl | F | Cl | F | 461 |
| 15 | H | 3-CH₃-1,2,4-oxadiazole | F | Cl | Cl | 465 |

-continued

| Ex. | R⁴ | R⁶ | R⁵ | R⁷ | R⁸ | LRMS (M + H⁺) |
|---|---|---|---|---|---|---|
| 16 | H | 5-CH₃-1,2,4-oxadiazole | F | F | Cl | 448 |
| 17 | Me | 5-CH₃-1,2,4-oxaidazole | F | F | F | 447 |
| 18 | Me | OCH₂CH₃ | Cl | Cl | Cl | 455 |
| 19 | H | 2-CH₃-2-tetrazol-5-yl | F | Cl | Cl | 465 |
| 20 | H | 2-CH₃-2H-tetrazol-5-yl | Cl | F | Cl | 465 |
| 21 | Me | 2-CH₃-2H-tetrazol-5-yl | Cl | F | H | 443 |
| 22 | H | 3-CH₃-1,2,4-oxadiazole | F | F | Cl | 448 |
| 23 | H | 2-CH₃-2H-tetrazol-5-yl | Cl | Cl | Cl | 481.1 |
| 24 | Me | 2-CH₃-2H-tetrazol-5-yl | Cl | F | F | 462 |
| 25 | H | CO₂CH₃ | F | Cl | Cl | 441 |
| 26 | Me | 5-CH₃-1,2,4-oxadiazole | F | Cl | F | 461 |
| 27 | Me | OCH₂CHF₂ | F | Cl | Cl | 477 |
| 28 | Me | 3-CH₃-1,2,4-oxadiazole | Cl | Cl | F | 479 |
| 29 | H | 2-CH₃-2H-tetrazol-5-yl | F | F | F | 433 |
| 30 | H | 5-CH₃-1,2,4-oxadiazole | F | Cl | Cl | 465 |
| 31 | H | CO₂CH₂CH₃ | F | Cl | Cl | 455 |
| 32 | H | 2-CH₃-2H-tetrazol-5-yl | Cl | F | F | 449 |
| 33 | H | 2-CH₃-2H-tetrazol-5-yl | Cl | Cl | F | 465 |
| 34 | H | 2-CH₃-2H-tetrazol-5-yl | F | Cl | F | 447 |
| 35 | H | OCH₂CHF₂ | F | Cl | Cl | 463 |
| 36 | H | 3-CH₃-1,2,4-oxadiazole | F | F | F | 433 |

Example 37

N-((1R)-1-{5-[5-chloro-3-fluoro-2-(2-methyl-2H-tetrazol-5-yl)phenyl]-3-fluoropyridin-2-yl}ethyl)-2-fluoro-1-hydroxycyclopentanecarboxamide

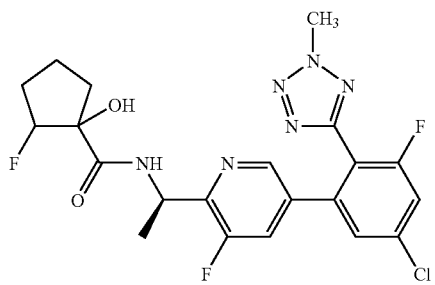

Methyl cyclopent-1-ene-1-carboxylate (30.0 g, 237.8 mmol) was dissolved in 20 mL of dichloromethane and 3-chloroperbenzoic acid (64.4 g, 373.3 mmol) was added. The reaction was allowed to stir vigorously for 2 hours. The reaction mixture was diluted with EtOAc and washed with 0.5 N NaOH. The organic layer was dried over sodium sulfate, filtered and concentrated to give 48.0 grams of methyl 6-oxabicyclo[3.1.0]hexane-1-carboxylate.

Methyl 6-oxabicyclo[3.1.0]hexane-1-carboxylate (2.10 g, 14.8 mmol) and N,N-diethyl-ethanamine trihydrofluoride (4.76 g, 29.5 mmol) were heated in a sealable Emrys microwave vessel with stir bar a microwave reactor at 180° C. for 30 minutes. The reaction mixture was diluted with dichloromethane and washed with saturated aqueous sodium bicarbonate solution. The organic layer was further washed with water and then brine. The organic layer was dried over sodium sulfate, filtered and concentrated to a crude oil, which was subjected to chromatography on silica gel eluting with 0 to 25% EtOAc in hexanes to afford racemic trans methyl-2-fluoro-1-hydroxycyclopentanecarboxylate.

The racemic trans methyl-2-fluoro-1-hydroxycyclopentanecarboxylate (0.285 g, 1.76 mmol) was dissolved in 21.3 mL of a 4:1 solution of THF:deionized water. A solution of 1 N NaOH was added to the reaction mixture, which was stirred for 1.5 hours. The reaction was acidified with 6 N HCl and extracted with EtOAc three times. The organic layers were combined, dried over sodium sulfate, filtered and concentrated to give racemic trans 2-fluoro-1-hydroxycyclopentanecarboxylic acid as a colorless oil.

To a mixture of the compound of Reference Example 4 (0.215 g, 6.13 mmol), racemic trans 2-fluoro-1-hydroxycyclopentanecarboxylic acid (90.8 mg, 0.61 mmol), and (1H-1,2,3-benzotriazol-1-yloxy)[tris(dimethylamino)]phosphonium hexafluorophosphate (0.380 g, 0.86 mmol) in 3 mL of dichloromethane was added triethylamine (0.155 g, 1.53 mmol). This reaction mixture was allowed to stir at ambient temperature for 1 hour. The reaction mixture was washed with water, 0.25 N HCl, and saturated aqueous sodium bicarbonate solution prior to drying over sodium sulfate. Filtration and solvent removal provided material which was subjected to chromatography on silica gel eluting with 0-40% EtOAc in hexanes to give a mixture of the two diastereomers. Subsequent preparatory TLC eluting with 40% EtOAc in hexanes yielded the title compound. Less polar diastereomer (beige solid): mass ion (ES+) of 481.0 for M+H$^+$: $^1$H NMR (500 MHz, CDCl$_3$) δ 8.11 (s, 1H), 7.66 (bs, NH), 7.35 (d, J=2.0 Hz, 1H), 7.34-7.25 (m, 2H), 5.48 (quint, J=6.8 Hz, 1H), 4.71 (dd, J=3.9 Hz, J=53.0 Hz, 1H), 4.33 (s, 3H), 4.20 (s, OH), 2.19-2.16 (m, 2H), 1.99-1.92 (m, 4H), 1.467 (d, J=6.8 Hz, 3H). More polar diastereomer: mass ion (ES+) of 481.0 for M+H$^+$: $^1$H NMR (500 MHz, CDCl$_3$) δ 8.13 (s, 1H), 7.483 (bs, NH), 7.35 (d, J=9.0 Hz, 1H), 7.28-7.24 (m, 2H), 5.47 (m, 1H), 4.79 (dd, J=3.4 Hz, J=53.0 Hz, 1H), 4.34 (s, 3H), 4.23 (s, OH), 2.26-1.91 (m, 6H), 1.46 (d, J=6.6 Hz, 3H).

Example 38

N-({5-[5-chloro-3-fluoro-2-(2-methyl-2H-tetrazol-5-yl)phenyl]-3-fluoropyridin-2-yl}methyl)-2-fluoro-1-hydroxycyclopentanecarboxamide

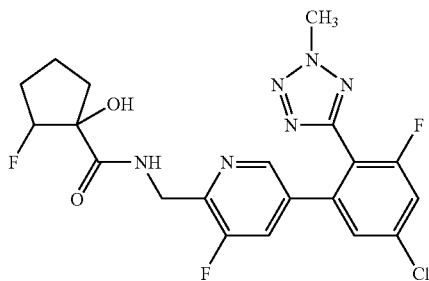

The title compound was prepared in a manner analogous to that described in Example 38, and separated into two enantionmers. LRMS (M+H$^+$): 466.

Example 39

N-((1R)-1-{5-[5-chloro-3-fluoro-2-(2-methyl-2H-tetrazol-5-yl)phenyl]-3-fluoropyridin-2-yl}ethyl)-3,3-difluoro-1-hydroxycyclopentanecarboxamide

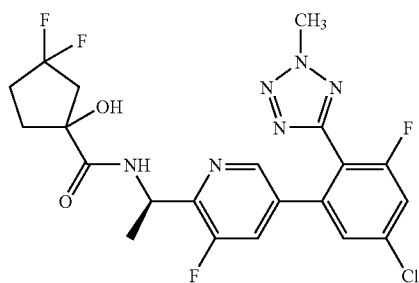

To a solution of 3-carboxycyclopentanone (640 mg, 5.0 mmol) in 8 mL of degassed DMF was added potassium carbonate (828 mg, 5.99 mmol) and benzyl bromide (0.65 mL, 5.49 mmol). After 4 hours at room temperature, the reaction mixture was poured into 50 mL of water and extracted 3 times with EtOAc. The combined organic layers were washed with water and dried over sodium sulfate. Filtration and solvent removal provided material that was subjected to silica gel chromatography eluting with 10% EtOAc in hexanes to yield benzyl 3-oxocyclopentanecarboxylate.

To a solution of benzyl 3-oxocyclopentanecarboxylate (1.03 g, 4.72 mmol) in 8 ml of 1,2-dichloroethane was added 3.34 g (7.55 mmol) of bis(2-methoxymethyl)amino-sulfur trifluoride. The mixture was heated at 50° C. for 20 hours and then slowly poured into 50 ml of saturated aqueous sodium bicarbonate solution. The mixture was extracted with one portion of chloroform and then two portions of ethyl acetate. The combined organic extracts were dried, filtered, concentrated, and subjected to silica gel chromatography eluting with 5-10% EtOAc in hexanes to yield benzyl 3,3-difluorocyclopentanecarboxylate.

A solution of benzyl 3,3-difluorocyclopentanecarboxylate (13.1 g, 54.7 mmol) in 274 ml of THF was cooled to −78° C. under nitrogen. Potassium bis(trimethylsilyl)amide (175 ml of 0.5 M toluene solution, 87.5 mmol) was added via syringe over 15 minutes. The mixture was stirred for one hour, and then a solution of 3-phenyl-2-(phenylsulfonyl)oxaziridine (17.1 g, 65.6 mmol) in 50 ml of THF was added dropwise over 2 minutes. After 30 minutes at −78° C., the reaction was quenched with the addition of 300 ml of saturated aqueous ammonium chloride solution. The reaction mixture was then warmed to room temperature, diluted with 100 ml of water, and extracted with EtOAc. The combined EtOAc extracts were washed with water and brine, and dried over sodium sulfate. Filtration and evaporation of solvent gave 35 g of an oily solid. The oily solid was stirred with 150 ml of chloroform and then filtered to remove the insoluble material. The filtrate was concentrated in vacuo and the residue was subjected to chromatography on silica gel eluting with 5 to 30% EtOAc in hexane to afford 8.2 g of racemic benzyl 3,3-difluoro-1-hydroxycyclopentanecarboxylate.

The racemic material (5.3 g) was then applied to a ChiralPak AD column (5 cm×50 cm, 20μ) to effect separation of enantiomers. The mobile phase gradient was 100% hexane to 15% ethanol in hexane over 1 hour, and the flow rate was 100 ml per minute. The ultraviolet detector was set at 250 nm. The (+)-enantiomer eluted first (retention time, 33.66 min) and the (−)-enantiomer eluted at 39.16 minutes.

To a solution of (+)-benzyl 3,3-difluoro-1-hydroxycyclopentanecarboxylate (1.8 g, 7.0 mmol) in 45 ml of EtOAc was added a suspension of 10% Palladium on Carbon (720 mg) in 5 ml of EtOAc. The mixture was stirred at room temperature under hydrogen atmosphere for 1 hour (balloon). The reaction mixture was filtered through a glass micropore filter to remove the catalyst and the filtrate was concentrated under vacuum to give (+)-3,3-difluoro-1-hydroxycyclopentanecarboxylic acid.

To a solution of the compound of Reference Example 4 (0.766 g, 2.18 mmol), (+)-3,3-difluoro-1-hydroxycyclopentanecarboxylic acid (0.454 g, 2.73 mmol), (1H-1,2,3-benzotriazol-1-yloxy)-[tris(dimethylamino)]phosphonium hexafluorophosphate (1.35 g, 3.06 mmol) in anhydrous dichloromethane (43 mL), was added triethylamine (0.553 g, 5.46 mmol). This reaction mixture was allowed to stir at ambient temperature for 1 hour. After the reaction was judged complete by LC/MS analysis, the volume of the reaction was reduced in vacuo. The residue was taken up in EtOAc, washed with water, 0.25 N HCl and saturated aqueous sodium bicarbonate solution. The organic extracts were dried over sodium sulfate, filtered, and concentrated. The crude residue was subjected to silica gel chromatography eluting with 0-50% EtOAc in hexanes to provide the title compound as a foam, which gave proton NMR spectra consistent with theory and a mass ion (ES+) of 499.2 for M+H$^+$: $^1$H NMR (500 MHz, CDCl$_3$) δ 8.13 (s, 1H), 7.96 (bd, NH), 7.34 (d, J=8.8 Hz, 1H), 7.26 (m, 2H), 5.41 (m, 1H), 4.342 (s, 3H), 2.82 (m, 1H), 2.46-2.25 (m, 4H), 1.92 (m, 1H), 1.45 (d, J=6.8 Hz, 3H).

The following compounds were prepared in a manner analogous to that described in Example 40; for each compound each of the two diastereomers was obtained and characterized.

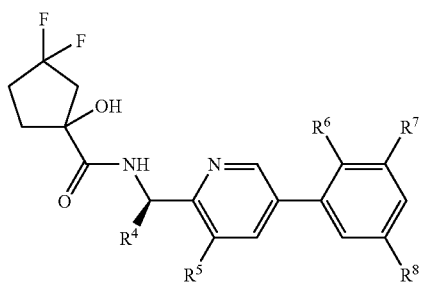

| Example | R$^4$ | R$^6$ | R$^5$ | R$^7$ | R$^8$ | LRMS (M + H$^+$) |
|---|---|---|---|---|---|---|
| 40 | H | CO$_2$CH$_3$ | F | Cl | Cl | 476 |
| 41 | H | 2-CH$_3$-2H-tetrazol-5-yl | F | F | Cl | 484 |
| 42* | Me | 2-H-tetrazol-5-yl | F | F | Cl | 484 |
| 43 | H | 3-CH$_3$-1,2,4-oxadiazole | F | F | Cl | 484 |
| 44 | H | 5-CH$_3$-1,2,4-oxadiazole | F | F | Cl | 484 |
| 45 | H | CO$_2$CH$_3$ | Cl | Cl | Cl | 493 |
| 46 | H | 3-CH$_3$-1,2,4-oxadiazole | Cl | F | Cl | 500 |
| 47 | H | 2-CH$_3$-2H-tetrazol-5-yl | Cl | F | Cl | 501 |
| 48 | H | 2-CH$_3$-2H-tetrazol-5-yl | F | Cl | Cl | 501 |
| 49 | H | 3-CH$_3$-1,2,4-oxadiazole | Cl | F | Cl | 501 |
| 50 | H | 5-CH$_3$-1,2,4-oxadiazole | Cl | F | Cl | 501 |
| 51 | Me | 5-CH$_2$F-1,2,3-triazole | F | F | Cl | 516 |
| 52 | H | 2-CH$_3$-2H-tetrazol-5-yl | Cl | Cl | Cl | 517 |

*one diastereomer made.

Example 53

N-((1R)-1-{5-[5-chloro-3-fluoro-2-(2-methyl-2H-tetrazol-5-yl)phenyl]-3-fluoropyridin-2-yl}ethyl)-1,3-dihydroxycyclopentanecarboxamide

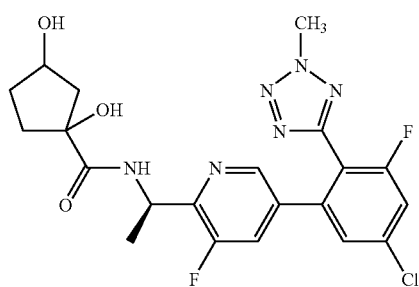

To a solution of cyclopent-3-ene-1-carboxylic acid (9.63 g, 85.88 mmol) in 143 mL of degassed DMF was added potassium carbonate (14.24 g, 103.06 mmol) and benzyl bromide (11.24 mL, 94.47 mmol). The mixture was stirred for 2 hours at ambient temperature, and then poured into 150 mL of water and extracted with ethyl acetate. The extracts were washed with water and brine, and dried over sodium sulfate. Filtration and concentration under vacuum afforded benzyl cyclopent-3-ene-1-carboxylate as an oil.

The benzyl cyclopent-3-ene-1-carboxylate (2.0 g, 9.89 mmol) was dissolved in 20 mL of THF and cooled to 0° C. under nitrogen. Borane-THF complex (0.95 mL, 9.89 mmol) was added via syringe and the mixture was stirred for 30 minutes at 0° C. Sodium perborate tetrahydrate solution (100 mL of 0.33 M aqueous solution) was added, and after 30 minutes the reaction mixture was extracted with ethyl acetate. The combined extracts were washed with water and brine and then dried over sodium sulfate. Filtration and concentration provided the crude product which was purified by chromatography on silica gel eluting with 10 to 30% EtOAc in hexanes to provide benzyl 3-hydroxycyclopentanecarboxylate.

To a solution of benzyl 3-hydroxycyclopentanecarboxylate (1.0 g, 4.54 mmol) in 9 ml of degassed DMF was added imidazole (0.34 g, 4.99 mmol) and tert-butyldimethylsilyl chloride (0.75 g, 4.99 mmol). The mixture was stirred at ambient temperature for 4 hours, and then poured into 70 mL of water, and extracted with ethyl acetate. The combined ethyl acetate extracts were washed with water and brine and then dried over sodium sulfate. Filtration and concentration afforded the crude product which was subjected to chromatography on silica gel eluting with 5% EtOAc in hexanes to give benzyl 3-{[tert-butyl(dimethyl)silyl]oxy}cyclopentanecarboxylate.

A solution of above benzyl ester (1.4 g, 4.19 mmol) was dissolved in 21 mL of THF and the solution was cooled to −78° C. Potassium bis(trimethylsilyl)amide (13.4 mL of 0.5 M solution in toluene) was added and the mixture was stirred at −78° C. for one hour. A THF solution (10 mL) of 3-phenyl-2-(phenylsulfonyl)oxaziridine (1.53 g, 5.86 mmol) was added and the reaction mixture was stirred for 40 minutes. After quenching with a saturated solution of aqueous ammonium chloride and warming to room temperature, the mixture was extracted with EtOAc. The combined organic layers were washed with water and brine and dried over sodium sulfate. Filtration and removal of solvent gave an crude product. The crude reaction product was stirred with 20 mL of chloroform, and then filtered to remove the insoluble material. The filtrate was concentrated under vacuum, and the residue was subjected to silica gel chromatography eluting with 5 to 10% EtOAc in hexanes) to provide benzyl 3-{[tert-butyl(dimethyl)silyl]oxy}-1-hydroxycyclopentanecarboxylate.

The above product (807 mg, 2.30 mmol) was dissolved in 12 mL of EtOAc. A suspension of 10% Palladium on carbon (300 mg in 3 mL of EtOAc) was added, and the mixture was stirred under an atmosphere of hydrogen for 35 minutes (balloon). The catalyst was removed by filtration, and the filtrate was concentrated under vacuum to afford 3-{[tert-butyl(dimethyl)silyl]oxy}-1-hydroxycyclopentanecarboxylic acid.

The above acid (300 mg, 1.15 mmol) and the compound of Reference Example 4 (491 mg, 1.27 mmol) were dissolved in 2 mL of DMF. HOBT (31 mg, 0.23 mmol) and EDCI (254 mg, 1.33 mmol) were added, and the mixture was made basic with triethylamine (117 mg, 1.15 mmol). After 1.5 hours at ambient temperature, 5 mL of water and 5 mL of 10% sodium bicarbonate were added, and the mixture was extracted with EtOAc. The combined organic layers were washed with water and brine, dried over sodium sulfate, filtered, and concentrated. The residue was dissolved in 10 mL of THF and 10 mL of 1 N HCl was added. The reaction mixture was stirred at ambient temperature for 1 hour, and then the pH of the reaction was adjusted to 8.5 by addition of saturated aqueous sodium bicarbonate solution. Extraction with EtOAc followed by washing of the combined extracts with brine and drying over sodium sulfate afforded crude product. Chromatography on silica gel eluting with 1 to 2% methanol in chloroform afforded the title compound as a racemic mixture of cis and trans isomers, which gave a proton NMR spectrum consistent with theory and a mass ion (ES+) of 479.2 for M+H$^+$: $^1$H NMR (500 MHz, CDCl$_3$) δ 8.21 (s, 1H), 7.35 (d, J=9 Hz, 1H), 7.26 (m, 2H), 5.44 (m, 1H), 4.35 (s, 3H), 2.43-1.82 (m, 6H), 1.46 (d, J=7 Hz, 3H).

Example 54

N-((1R)-1-{5-[5-chloro-3-fluoro-2-(2-methyl-2H-tetrazol-5-yl)phenyl]-3-fluoropyridin-2-yl}ethyl)-1-hydroxy-3-oxocyclopentanecarboxamide

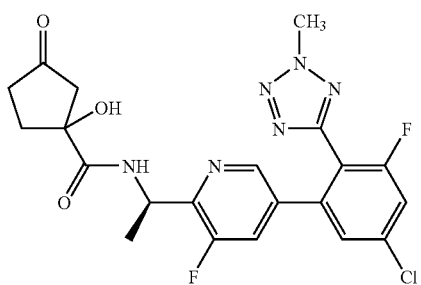

To a solution of the product of previous Example 53 (100 mg, 0.209 mmol) in 1.5 mL of methylene chloride was added 300 mg of crushed molecular sieves. N-methylmorpholine-N-oxide (37 mg, 0.313 mmol) and tetrapropylammonium perruthenate (4 mg, 0.01 mmol) were then added, and the mixture was allowed to stir at ambient temperature for 2.5 hours. The reaction mixture was then diluted with dichloromethane and filtered to remove molecular sieves. The filtrate was washed with water and brine, and dried over sodium sulfate. Filtration and concentration provided the crude product. Chromatography on silica gel eluting with 5% methanol in chloroform, afforded the title compound as a racemic mixture, which gave a proton NMR spectrum consistent with theory and a mass ion (ES+) of 477.2 for M+H$^+$: $^1$H NMR (400 MHz, CDCl$_3$) δ 8.11 (m, 2H), 7.35 (d, J=6 Hz, 1H), 7.26 (m, 2H), 5.43 (m, 1H), 4.36 (s, 3H), 2.52 (m, 3H), 1.45 (d, J=6.6 Hz, 3H).

Example 55

N-((1R)-1-{5-[5-chloro-3-fluoro-2-(2-methyl-2H-tetrazol-5-yl)phenyl]-3-fluoropyridin-2-yl}ethyl)-3-fluoro-1-hydroxycyclopentanecarboxamide

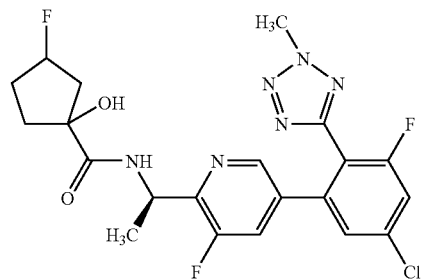

To a solution of bis(2-methoxymethyl)amino-sulfur trifluoride (1.14 g, 5.14 mmol) in 1 ml of methylene chloride at −78° C. was added benzyl 3-hydroxycyclopentanecarboxylate (0.45 g, 2.02 mmol) in 3 mL of methylene chloride. The reaction mixture was allowed to slowly warm to room temperature. After 30 minutes at room temperature, the reaction mixture was poured in 30 mL of saturated aqueous sodium bicarbonate solution and extracted with chloroform. The combined organic extracts were dried, filtered, concentrated, and subjected to silica gel chromatography eluting with 5-10% EtOAc in hexanes to yield benzyl 3-fluorocyclopentanecarboxylate.

The title compound was prepared as a racemic mixture of cis and trans isomers in a manner analogous to that described in Example 39. LRMS (M+H$^+$):480.

Example 56

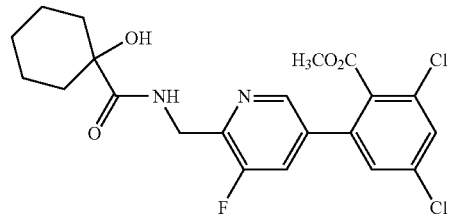

The title compound was prepared in a manner analogous to that described in Example 1. LRMS (M+H$^+$): 469.

Example 57

N-((1R)-1-{5-[5-chloro-3-fluoro-2-(2-methyl-2H-tetrazol-5-yl)phenyl]-3-fluoropyridin-2-yl}ethyl)-4,4-difluoro-1-hydroxycyclohexanecarboxamide

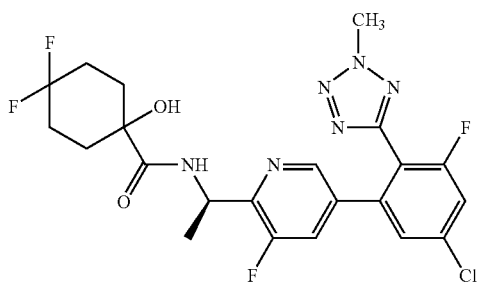

To a solution of 4-hydroxycyclohexane carboxylic acid (19.95 g, 138.4 mmol) in 100 mL of degassed DMF was added potassium carbonate (21.0 g, 152.2 mmol) and benzyl bromide (15.61 mL, 131.4 mmol). After 16 hours at room temperature, the reaction mixture was poured into 500 mL of water and extracted 3 times with EtOAc. The combined organic layers were washed with water and brine prior to drying over sodium sulfate. Filtration and solvent removal provided benzyl 4-hydroxycyclohexane carboxylate as a clear oil.

To a solution of benzyl 4-hydroxycyclohexane carboxylate (32.1 g, 137.2 mmol) in 400 mL of dichloromethane was added pyridinium chlorochromate (68.8 g, 274.0 mmol) in portions over 10 minutes. After two hours, the reaction was filtered through a large plug of silica gel eluting with 30% ethyl acetate in hexane to afford benzyl 4-oxocyclohexane carboxylate as an oil.

Benzyl 4-oxocyclohexane carboxylate was dissolved in 8 ml of 1,2-dichloroethane and 3.34 g (7.55 mmol) of bis(2-methoxymethyl)amino-sulfur trifluoride was added. The mixture was allowed to stir at room temperature overnight and then slowly poured into 50 ml of saturated aqueous sodium bicarbonate solution. The reaction mixture was extracted with one portion of chloroform and then two portions of ethyl acetate. The combined organic extracts were dried, filtered, concentrated, and subjected to silica gel chromatography eluting with 0-5% EtOAc in hexanes to afford benzyl 4-fluoro-cyclohex-3-ene-1-carboxylate and benzyl 4,4-difluorocyclohexanecarboxylate.

A solution of benzyl-4,4-difluorocyclohexanecarboxylate (6.5 g, 25.56 mmol) in 128 ml of THF was cooled to −78° C. under nitrogen. Potassium bis(trimethylsilyl)amide (76.7 mL of 0.5 M solution in toluene) was added, and the mixture was stirred at −78° C. for one hour. A THF solution (35 mL) of 3-phenyl-2-(phenylsulfonyl)oxaziridine (9.35 g, 35.79 mmol) was added, and the reaction was stirred for 40 minutes. After quenching with a saturated aqueous ammonium chloride solution and warming to room temperature, the reaction mixture was extracted with EtOAc. The combined organic layers were washed with water and brine prior to drying over sodium sulfate. Filtration and removal of solvent provided crude product which was stirred with 100 mL of chloroform, and then filtered to remove the insoluble material. The filtrate was concentrated under vacuum and the residue was subjected to silica gel chromatography eluting with 5 to 20% EtOAc in hexane to afford benzyl 4,4-difluoro-1-hydroxycyclohexanecarboxylate.

Benzyl 4,4-difluoro-1-hydroxycyclohexanecarboxylate (2.76 g, 10.21 mmol) was dissolved in 68 mL of EtOAc and a suspension of 10% Palladium on Carbon (1.1 g in 5 mL of EtOAc) was added. The mixture was stirred at room temperature under at atmosphere of hydrogen for 45 minutes (balloon), and the reaction mixture was filtered through a glass micropore filter and concentrated under vacuum to provide 4,4-difluoro-1-hydroxy-cyclohexanecarboxylic acid.

A mixture of 4,4-difluoro-1-hydroxy-cyclohexanecarboxylic acid (324 mg, 1.8 mmol) and the compound of Reference Example 4 (632 mg, 1.8 mmol) was dissolved in 3.6 ml of degassed DMF. HOBT (58 mg, 0.43 mmol) and EDCI (449 mg, 2.34 mmol) were added, and the reaction mixture was made basic with triethylamine (182 mg, 1.8 mmol). After 1 hour at ambient temperature, 20 ml of water and 2 ml of 10% aqueous sodium bicarbonate solution were added and the mixture was extracted with EtOAc. The combined organic extracts were washed with water and brine, and dried over sodium sulfate, filtered, and concentrated. The crude material was subjected to silical gel chromatography eluting with 10 to 30% EtOAc in hexanes to provide the title compound as a white solid which gave a proton NMR spectrum consistent with theory and a mass ion (ES+) of 513.0 for M+H$^+$: $^1$H NMR (500 MHz, CDCl$_3$) δ 8.14 (s, 1H), 7.67 (d, J=7 Hz, 1H), 7.35 (d, J=10 Hz, 1 H), 7.28 (m, 2H), 5.41 (m, 1H), 4.36 (s, 3H), 2.88 (s, 1H), 2.12 (m, 6H), 1.76 (m, 2H), 1.44 (d, J=7 Hz, 3H).

The following compounds were prepared in a manner analogous to that described in Example 57:

| Example | R$^4$ | R$^6$ | R$^5$ | R$^7$ | R$^8$ | LRMS (M + H$^+$) |
|---|---|---|---|---|---|---|
| 58 | H | CO$_2$CH$_3$ | F | F | Cl | 474 |
| 59 | H | CO$_2$CH$_3$ | F | Cl | Cl | 491 |
| 60 | H | 2-CH$_3$-2H-tetrazol-5-yl | F | F | Cl | 498 |
| 61 | H | 2-H-tetrazol-5-yl | F | F | Cl | 498 |
| 62 | H | CO$_2$CH$_3$ | F | Cl | Cl | 505 |
| 63 | H | CO$_2$CH$_3$ | Cl | F | Cl | 505 |
| 64 | H | CO$_2$CH$_3$ | Cl | Cl | Cl | 507 |
| 65 | Me | 5-CH$_2$-1,2,3-triazole | F | F | Cl | 511 |
| 66 | H | 2-CH$_3$-2H-tetrazol-5-yl | Cl | F | Cl | 515 |
| 67 | H | 2-CH$_3$-2H-tetrazol-5-yl | F | Cl | Cl | 515 |
| 68 | H | CO$_2$CH$_3$ | Cl | Cl | Cl | 521 |
| 69 | H | 2-CH$_3$-2H-tetrazol-5-yl | Cl | F | Cl | 529 |
| 70 | Me | 5-CH$_3$-1,2,4-oxaidazole | Cl | F | Cl | 529 |
| 71 | H | 2-CH$_3$-2H-tetrazol-5-yl | F | Cl | Cl | 529 |
| 72 | Me | 5-CH$_2$F-1,2,3-triazole | F | F | Cl | 529 |
| 73 | Me | 5-CH$_2$F-1,2,4-oxadiazole | F | F | Cl | 530 |
| 74 | H | 2-CH$_3$-2H-tetrazol-5-yl | Cl | Cl | Cl | 545 |
| 75 | H | 2-CH$_2$CHF$_2$-2H-tetrazol-5-yl | F | F | Cl | 562 |
| 76 | H | 2-CHF$_2$-2H-tetrazol-5-yl | F | F | Cl | 548 |

Example 77

N-((1R)-1-{5-[5-chloro-3-fluoro-2-(2-methyl-2H-tetrazol-5-yl)phenyl]-3-fluoropyridin-2-yl}ethyl)-4,4-difluoro-1-hydroxycyclohexanecarboxamide

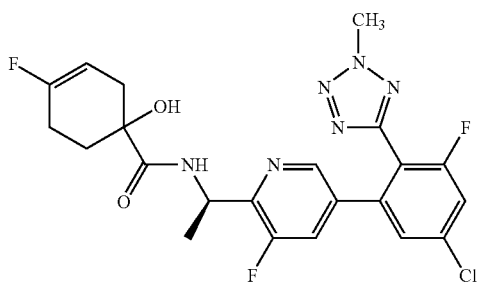

A mixture of benzyl 4-fluorocyclohex-3-ene-1-carboxylate (1.77 g, 7.56 mmol) and 38 mL of THF was stirred vigorously and cooled to −78° C. To the reaction mixture was added dropwise over 15 minutes a solution of 0.5 M potassium bis(trimethylsilyl)amide in toluene (2.56 g, 12.8 mmol. The reaction mixture was allowed to stir vigorously for 1 hour. In a separate flask, 3-phenyl-2-(phenyl-sulfonyl)oxaziridine (2.17 g, 8.31 mmol) was dissolved in 2 mL of THF. The oxaziridine solution was then added to the reaction mixture dropwise. The reaction mixture was allowed to stir for 2 hours more and quenched with a saturated aqueous ammonium chloride solution. The biphasic reaction was separated and the aqueous layer was extracted three times with EtOAc. The combined organic extracts were dried over sodium sulfate, filtered, concentrated and purified by chromatography on silica gel, eluting with 0-15% EtOAc in hexanes, to give benzyl 4-fluoro-1-hydroxycyclohex-3-ene-1-carboxylate as an oil.

Benzyl 4-fluoro-1-hydroxycyclohex-3-ene-1-carboxylate (0.554 g, 2.21 mmol) was dissolved in 27.5 mL of a 4:1 solution of THF:deionized water. A solution of 1 N NaOH was added to the reaction mixture. After stirring for 1.5 hours, the reaction mixture was acidified with 6 N HCl and extracted with EtOAc three times. The organic extracts were combined, washed with water, dried over sodium sulfate, filtered and concentrated to give 4-fluoro-1-hydroxycyclohex-3-ene-1-carboxylic acid as an oil.

To a mixture of the compound of Reference Example 4 (0.192 g, 0.547 mmol), 4-fluoro-1-hydroxycyclohex-3-ene-1-carboxylic acid (0.114 g, 0.71 mmol), (1H-1,2,3-benzotriazol-1-yloxy)[tris-(dimethylamino)]phosphonium hexafluorophosphate (0.339 g, 0.77 mmol) in 5 mL of dichloromethane was added triethylamine (0.138 g, 1.37 mmol). The reaction mixture was allowed to stir at ambient temperature for 1 hour. After the reaction was judged complete by LC/MS analysis, the volume of the reaction was reduced in vacuo. The residue was taken up in EtOAc and washed in succession with water, 0.25 N HCl and saturated aqueous sodium bicarbonate solution prior to drying over sodium sulfate. Filtration and solvent removal provided material which was subjected to chromatography on silica gel eluting with 0-50% EtOAc in hexanes to yield a mixture of diastereomers of N-((1R)-1-{5-[5-chloro-3-fluoro-2-(2-methyl-2H-tetrazol-5-yl)phenyl]-3-fluoropyridin-2-yl}ethyl)-4-fluoro-1-hydroxycyclohex-3-ene-1-carboxamide, which gave a proton NMR spectrum consistent with theory and a mass ion (ES+) of 493.1 for M+H$^+$: $^1$H NMR (500 MHz, CDCl$_3$) δ 8.12 (s, 1H), 8.03 (bd, J=7.1 Hz, NH), 7.35 (d, J=8.9 Hz, 1H), 7.28-7.25 (m, 2H), 5.43 (quint, J=6.7 Hz, 1H), 5.16 (d, J=13.4 Hz, 1H), 4.35 (s, 3H), 2.79 (d, J=17.8 Hz, 1H), 2.68 (s, OH), 2.43 (m, 1H), 2.26 (m, 1H), 2.21-2.10 (m, 2H), 1.91 (m, 1H), 1.45 (d, J=6.8 Hz, 3H).

The mixture of diastereomers was separated on a ChiralPak AD column (5 cm×50 cm, 20 m). The mobile phase was 20% isopropanol in hexanes, and the flow rate was 100 ml per minute. The ultraviolet detector was set at 260 nm.

The following compounds were prepared as a racemic or diastereomeric mixture in a manner analogous to that described in Example 77.

| Example | R$^4$ | R$^6$ | R$^5$ | R$^7$ | R$^8$ | LRMS (M + H$^+$) |
|---|---|---|---|---|---|---|
| 78 | H | 2-CH$_2$-2H-tetrazol-5-yl | F | F | Cl | 479 |
| 79 | Me | CO$_2$CH$_3$ | F | F | Cl | 484 |

Example 80

N-((1R)-1-{5-[5-chloro-3-fluoro-2-(2-methyl-2H-tetraazol-5-yl)phenyl]-3-fluoropyridin-2-yl}ethyl)-4,4-difluoro-1,2-dihydroxycyclohexanecarboxamide

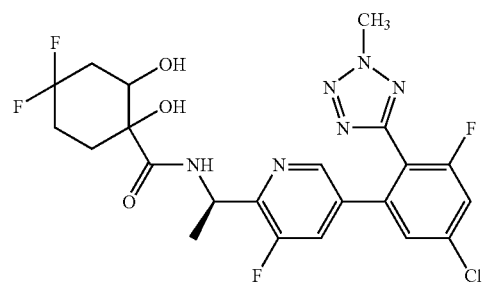

To a solution of benzyl 4,4-difluoro-1-hydroxycyclohexanecarboxylate (1.8 g, 6.66 mmol) in 13 ml of pyridine was added phosphorous oxychloride (1.12 g, 7.33 mmol). The resulting solution was stirred under nitrogen at room temperature for 18 hours, and then poured into 70 mL of saturated ammonium chloride solution and extracted with ethyl acetate. The combined ethyl acetate extracts were washed with 2 molar hydrochloric acid solution and brine and then dried over sodium sulfate. Filtration and concentration under vacuum afforded the crude product which was purified by chromatography on silica gel eluting 2% ethyl acetate in hexanes to give benzyl 4,4-difluorocyclohex-1-ene-1-carboxylate as an oil.

To a solution of the above ester (0.58 g, 2.29 mmol) in 6 mL of methanol and 0.5 mL of THF was added 2.5 mL of 1 molar sodium hydroxide solution. The solution was stirred for 4 hours at ambient temperature, and then the pH was adjusted to 6 by the addition of 2 M HCl. The reaction mixture was men concentrated under vacuum, and the residue was azeotroped with toluene to provide 4,4-difluorocyclohex-1-ene-1-carboxylic acid an oily solid.

The above carboxylic acid (223 mg, 1.37 mmol) and the compound of Reference Example 4 (482 mg, 1.37 mmol) were dissolved in 2.3 mL of degassed DMF. HOBT (21 mg, 0.14 mmol) and EDCI (303 mg, 1.58 mmol) were added, and the mixture was made basic with triethylamine (139 mg. 1.37 mmol). After 20 hours at ambient temperature, 10 mL of water and 1 mL of 10% sodium bicarbonate were added and the mixture was extracted with EtOAc. The combined organic layers were washed with water and brine, and then dried over sodium sulfate. Filtration and removal of solvent provided the crude product which was subjected to chromatography on silica gel eluting with 5 to 50% EtOAc in hexanes to give N-((1R)-1-{5-[5-chloro-3-fluoro-2-(2-methyl-2H-tetrazol-5-yl)phenyl]-3-fluoropyridin-2-yl}ethyl)-4,4-difluorocyclohex-1-ene-1-carboxamide To a solution of the above carboxamide (77 mg, 0.156 mmol) in 0.5 mL of acetone and 0.5 mL of water was added NMO (22 mg, 0.187 mmol) and osmium tetroxide (8 mg, 0.032 mmol). The mixture was stirred at ambient temperature for 3 hours, and then acetone was removed under reduced pressure. The residue was taken up in 50 mL of EtOAc and washed with 10% sodium bisulfite and brine, and then dried over sodium sulfate. Filtration and removal of solvent afforded the crude product which was chromatographed on preparative layer plates eluting with 45% EtOAc in hexanes to provide two diastereomers of the title compound. Purity of the less polar diastereomer was determined by LC/MS (ES MS, M+H$^+$ found 529.0) and proton NMR (500 MHz, CDCl$_3$) δ 7.99 (s, 1H), 7.41 (d, J=7 Hz, 1H), 7.34 (d, J=8 Hz, 1H), 7.16 (m, 2H), 5.34 (m, 1H), 4.36 (s, 3H), 4.25 (m, 1H), 2.34 (m, 1H), 2.00 (m, 4H), 1.47 (d, J=7 Hz, 3H). Purity of the more polar diastereomer was determined by LC/MS (ES MS, M+H$^+$ found 529.0) and proton NMR (500 MHz, CDCl$_3$) δ 8.12 (s, 1H), 7.9 (d, J=7.6 Hz, 1H), 7.35 (d, J=9 Hz, 1 H), 5.39 (m, 1H), 4.45 (m, 1H), 4.36 (s, 3H), 2.64 (d, J=5.6 Hz, 1H), 2.35 (m, 1H), 2.05 (m, 3H), 1.45 (d, J=6.8 Hz, 3H).

Example 81

N-({5-[5-Chloro-3-fluoro-2-(2-methyl-2H-tetrazol-5-yl)phenyl]-3-fluoropyridin-2-yl}-methyl)-1,2-dihydroxycyclopentanecarboxamide

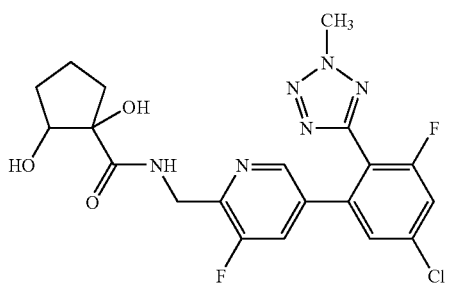

The title compound was prepared in a manner analogous to that described in Example 80. LRMS (M+H$^+$): 464.

What is claimed is:

1. A compound having the formula (I):

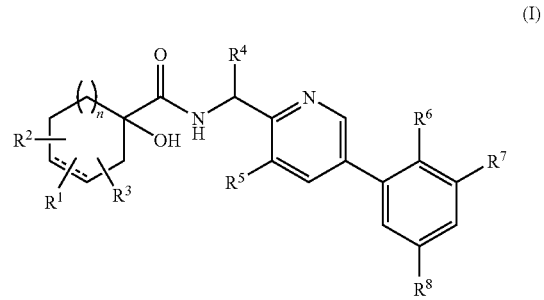

(I)

or a pharmaceutically acceptable salt thereof, wherein
 ⁓ is a single or double bond;
R$^1$, R$^2$, and R$^3$ are each independently selected from H, halogen and OH; or
R$^1$ and R$^2$ attached to the same carbon atom together represent oxo;
R$^4$ is H or methyl;
R$^5$ is Cl or F;
R$^6$ is selected from 2-methyltetrazol-5-yl, 5-methyl-1,2,4-oxadiazol-3-yl, 3-methyl,2,4-oxadiazol-5-yl, 5-halomethyl-1,2,4-oxadiazol-3-yl, 3-halomethyl-1,2,4-oxadiazol-5-yl, tetrazol-5-yl, 5-halomethyl-1,2,3-triazolyl, and 5-methyl-1,2,3-triazolyl;
R$^7$ and R$^8$ are each independently Cl or F; and
n is 0 or 1.

2. A compound of claim 1 wherein at least one of R$^1$, R$^2$, and R$^3$ is a fluorine atom.

3. A compound of claim 1 wherein n is 0.

4. A compound of claim 1 wherein n is 1.

5. A compound of claim 1 wherein R$^6$ is 2-methyl-tetrazol-5-yl.

6. pharmaceutical composition comprising a therapeutically effective amount of a compound of formula (I) or a pharmaceutically acceptable salt thereof, and a pharmaceutically acceptable carrier.

7. A compound of claim 1 selected from the group consisting of:

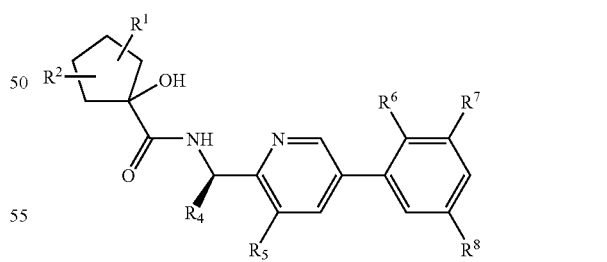

| R1/R2 | R$^4$ | R$^6$ | R$^5$ | R$^7$ | R$^8$ |
|---|---|---|---|---|---|
| H/H | H | 2-CH$_3$-2H-tetrazol-5-yl | F | F | Cl |
| H/H | Me | 5-CH$_2$F-1,2,4-oxadiazole | F | F | Cl |
| H/H | Me | 3-CH$_3$-1,2,4-oxadiazole | F | Cl | Cl |
| H/H | Me | 3-CH$_3$-1,2,4-oxadiazole | F | Cl | F |
| H/H | Me | 2-CH$_3$-2H-tetrazol-5-yl | F | F | Cl |
| H/H | Me | 2-CH$_3$-2H-tetrazol-5-yl | F | F | F |
| H/H | Me | 5-CH$_3$-1,2,4-oxadiazole | Cl | F | Cl |
| H/H | Me | 5-CH$_3$-1,2,4-oxadiazole | F | Cl | Cl |
| H/H | Me | 3-CH$_3$-1,2,4-oxadiazole | F | Cl | Cl |

-continued

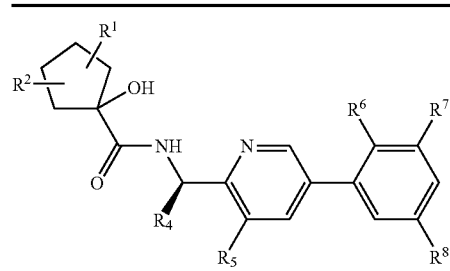

| R1/R2 | R4 | R6 | R5 | R7 | R8 |
|---|---|---|---|---|---|
| H/H | Me | 2-CH₃-2H-tetrazol-5-yl | Cl | Cl | Cl |
| H/H | Me | 2-CH₃-2H-tetrazol-5-yl | F | Cl | Cl |
| H/H | Me | 2-CH₃-2H-tetrazol-5-yl | F | Cl | F |
| H/H | H | 3-CH₃-1,2,4-oxadiazole | F | Cl | Cl |
| H/H | H | 5-CH₃-1,2,4-oxadiazole | F | F | Cl |
| H/H | Me | 5-CH₃-1,2,4-oxadiazole | F | F | F |
| H/H | H | 2-CH₃-2H-tetrazol-5-yl | F | Cl | Cl |
| H/H | H | 2-CH₃-2H-tetrazol-5-yl | Cl | F | Cl |
| H/H | Me | 2-CH₃-2H-tetrazol-5-yl | Cl | F | H |
| H/H | H | 3-CH₃-1,2,4-oxadiazole | F | F | Cl |
| H/H | H | 2-CH₃-2H-tetrazol-5-yl | Cl | Cl | Cl |
| H/H | Me | 2-CH₃-2H-tetrazol-5-yl | Cl | F | F |
| H/H | Me | 5-CH₃-1,2,4-oxadiazole | F | Cl | F |
| H/H | Me | 3-CH₃-1,2,4-oxadiazole | Cl | Cl | F |
| H/H | H | 2-CH₃-2H-tetrazol-5-yl | F | F | F |
| H/H | H | 5-CH₃-1,2,4-oxadiazole | F | Cl | Cl |
| H/H | H | 2-CH₃-2H-tetrazol-5-yl | Cl | F | F |
| H/H | H | 2-CH₃-2H-tetrazol-5-yl | Cl | Cl | F |
| H/H | H | 2-CH₃-2H-tetrazol-5-yl | F | Cl | F |
| H/H | H | 3-CH₃-1,2,4-oxadiazole | F | F | F |
| 2-F/H | Me | 2-CH₃-2H-tetrazol-5-yl | F | F | Cl |
| 2-F/H | H | 2-CH₃-2H-tetrazol-5-yl | F | F | Cl |
| 3-F/3-F | Me | 2-CH₃-2H-tetrazol-5-yl | F | F | Cl |
| 3-F/3-F | H | 2-CH₃-2H-tetrazol-5-yl | F | F | Cl |
| 3-F/3-F | Me | 2H-tetrazol-5-yl | F | F | Cl |
| 3-F/3-F | H | 3-CH₃-1,2,4-oxadiazole | F | F | Cl |
| 3-F/3-F | H | 5-CH₃-1,2,4-oxadiazole | F | F | Cl |
| 3-F/3-F | H | 3-CH₃-1,2,4-oxadiazole | Cl | F | Cl |
| 3-F/3-F | H | 2-CH₃-2H-tetrazol-5-yl | Cl | F | Cl |
| 3-F/3-F | H | 2-CH₃-2H-tetrazol-5-yl | F | Cl | Cl |
| 3-F/3-F | H | 3-CH₃-1,2,4-oxadiazole | Cl | F | Cl |
| 3-F/3-F | H | 5-CH₃-1,2,4-oxadiazole | Cl | F | Cl |
| 3-F/3-F | Me | 5-CH₂F-1,2,3-triazole | F | F | Cl |
| 3-F/3-F | H | 2-CH₃-2H-tetrazol-5-yl | Cl | Cl | Cl |
| 3-OH/H | Me | 2-CH₃-2H-tetrazol-5-yl | F | F | Cl |
| oxo | Me | 2-CH₃-2H-tetrazol-5-yl | F | F | Cl |
| 3-F/H | Me | 2-CH₃-2H-tetrazol-5-yl | F | F | Cl |
| 2-OH/H | H | 2-CH₃-2H-tetrazol-5-yl | F | F | Cl |

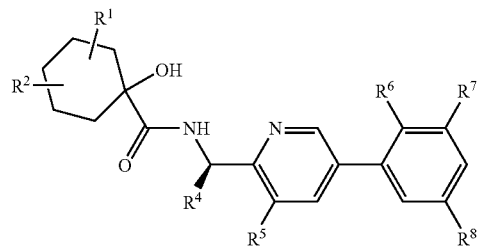

| R1/R2 | R4 | R6 | R5 | R7 | R8 |
|---|---|---|---|---|---|
| 4-F/4-F | Me | 2-CH₃-2H-tetrazol-5-yl | F | F | Cl |
| 4-F/4-F | H | 2-CH₃-2H-tetrazol-5-yl | F | F | Cl |
| 4-F/4-F | H | 2H-tetrazol-5-yl | F | F | Cl |
| 4-F/4-F | Me | 5-CH₃-1,2,3-triazole | F | F | Cl |
| 4-F/4-F | H | 2-CH₃-2H-tetrazol-5-yl | Cl | F | Cl |
| 4-F/4-F | H | 2-CH₃-2H-tetrazol-5-yl | F | Cl | Cl |
| 4-F/4-F | H | 2-CH₃-2H-tetrazol-5-yl | Cl | F | Cl |
| 4-F/4-F | Me | 5-CH₃-1,2,4-oxadiazole | Cl | F | Cl |
| 4-F/4-F | H | 2-CH₃-2H-tetrazol-5-yl | F | Cl | Cl |
| 4-F/4-F | Me | 5-CH₂F-1,2,3-triazole | F | F | Cl |
| 4-F/4-F | Me | 5-CH₂F-1,2,4-oxadiazole | F | F | Cl |
| 4-F/4-F | H | 2-CH₃-2H-tetrazol-5-yl | Cl | Cl | Cl |
| 4-F/4-F | H | 2-CH₂CHF₂-2H-tetrazol-5-yl | F | F | Cl |
| 4-F/4-F | H | 2-CHF₂-2H-tetrazol-5-yl | F | F | Cl |

N-((1R)-1-{5-[5-chloro-3-fluoro-2-(2-methyl-2H-tetrazol-5-yl)phenyl]-3-fluoropyridin-2-yl}ethyl)-4,4-difluoro-1-hydroxycyclohexanecarboxamide;

N-({5-[5-chloro-3-fluoro-2-(2-methyl-2H-tetrazol-5-yl)phenyl]-3-fluoropyridin-2-yl}methyl)-4,4-difluoro-1-hydroxycyclohexanecarboxamide; and N-((1R)-1-{5-[5-chloro-3-fluoro-2-(2-methyl-2H tetrazol-5-yl)phenyl]-3-fluoropyridin-2-yl}ethyl)-4,4-difluoro-1,2-dihydroxycyclohexanecarboxamide;

or a pharmaceutically acceptable salt thereof.

* * * * *